(12) United States Patent
Gropp et al.

(10) Patent No.: US 8,129,559 B2
(45) Date of Patent: Mar. 6, 2012

(54) PROCESS FOR PREPARING CYANOHYDRINS AND THEIR USE IN THE PREPARATION OF ALKYL ESTERS OF METHACRYLIC ACID

(75) Inventors: Udo Gropp, Bad Endorf (DE); Robert Weber, Alsbach-Haehnlein (DE); Thomas Schaefer, Buettelborn (DE); Andreas Perl, Bobenheim-Roxheim (DE); Rudolf Sing, Worms (DE); Thomas Mertz, Bensheim (DE)

(73) Assignee: Evonik Röhm GmbH, Darmstadt (DE)

( * ) Notice: Subject to any disclaimer, the term of this patent is extended or adjusted under 35 U.S.C. 154(b) by 303 days.

(21) Appl. No.: 12/515,545

(22) PCT Filed: Aug. 31, 2007

(86) PCT No.: PCT/EP2007/059112
§ 371 (c)(1),
(2), (4) Date: May 20, 2009

(87) PCT Pub. No.: WO2008/068065
PCT Pub. Date: Jun. 12, 2008

(65) Prior Publication Data
US 2010/0076214 A1    Mar. 25, 2010

(30) Foreign Application Priority Data
Dec. 8, 2006  (DE) .......................... 10 2006 058 249

(51) Int. Cl.
C07C 253/00    (2006.01)
(52) U.S. Cl. ...................................................... 558/351
(58) Field of Classification Search .................... 558/351
See application file for complete search history.

(56) References Cited

U.S. PATENT DOCUMENTS

| | | | |
|---|---|---|---|
| 4,312,837 | A | 1/1982 | Papp et al. |
| 6,030,534 | A | 2/2000 | De Lima |
| 6,180,831 | B1 | 1/2001 | Weber et al. |
| 6,417,385 | B1 | 7/2002 | Boerner et al. |
| 6,596,251 | B2 | 7/2003 | Schaefer et al. |
| 6,613,868 | B2 | 9/2003 | Kauth et al. |
| 6,743,407 | B2 | 6/2004 | Schaefer et al. |
| 6,977,310 | B2 | 12/2005 | Ackermann et al. |
| 6,979,432 | B2 | 12/2005 | Schaefer et al. |
| 7,014,821 | B2 | 3/2006 | Hottovy et al. |
| 7,423,173 | B2 | 9/2008 | Krill et al. |
| 7,429,370 | B2 | 9/2008 | Von Hippel et al. |
| 2002/0081254 | A1 | 6/2002 | Boger |
| 2003/0147791 | A1 | 8/2003 | Ding et al. |
| 2006/0165566 | A1 | 7/2006 | Kelm |
| 2007/0149811 | A1 | 6/2007 | Schleep et al. |
| 2008/0194862 | A1 | 8/2008 | Ackermann et al. |
| 2008/0194875 | A1 | 8/2008 | Ackermann et al. |
| 2009/0149674 | A1 | 6/2009 | Schleep et al. |

FOREIGN PATENT DOCUMENTS

| | | |
|---|---|---|
| CA | 1117133 | 1/1982 |
| DE | 29 27 979 | 1/1980 |
| EP | 0 022 138 | 1/1981 |
| EP | 1 666 451 | 6/2006 |
| WO | 00 64861 | 11/2000 |
| WO | 02 051534 | 7/2002 |
| WO | 2005 028097 | 3/2005 |

OTHER PUBLICATIONS

Office Action issue Apr. 7, 2011 in Russian Patent Application No. 2009 125 686 (with German language translation).

*Primary Examiner* — Rebecca Anderson
*Assistant Examiner* — Samantha Shterengarts
(74) *Attorney, Agent, or Firm* — Oblon, Spivak, McClelland, Maier & Neustadt, L.L.P.

(57) ABSTRACT

The invention relates to a process for preparing acetone cyanohydrin and to a process for preparing alkyl methacrylates, in which an acetone cyanohydrin as can be prepared in accordance with the present invention is used.

27 Claims, 7 Drawing Sheets

Figure 1:
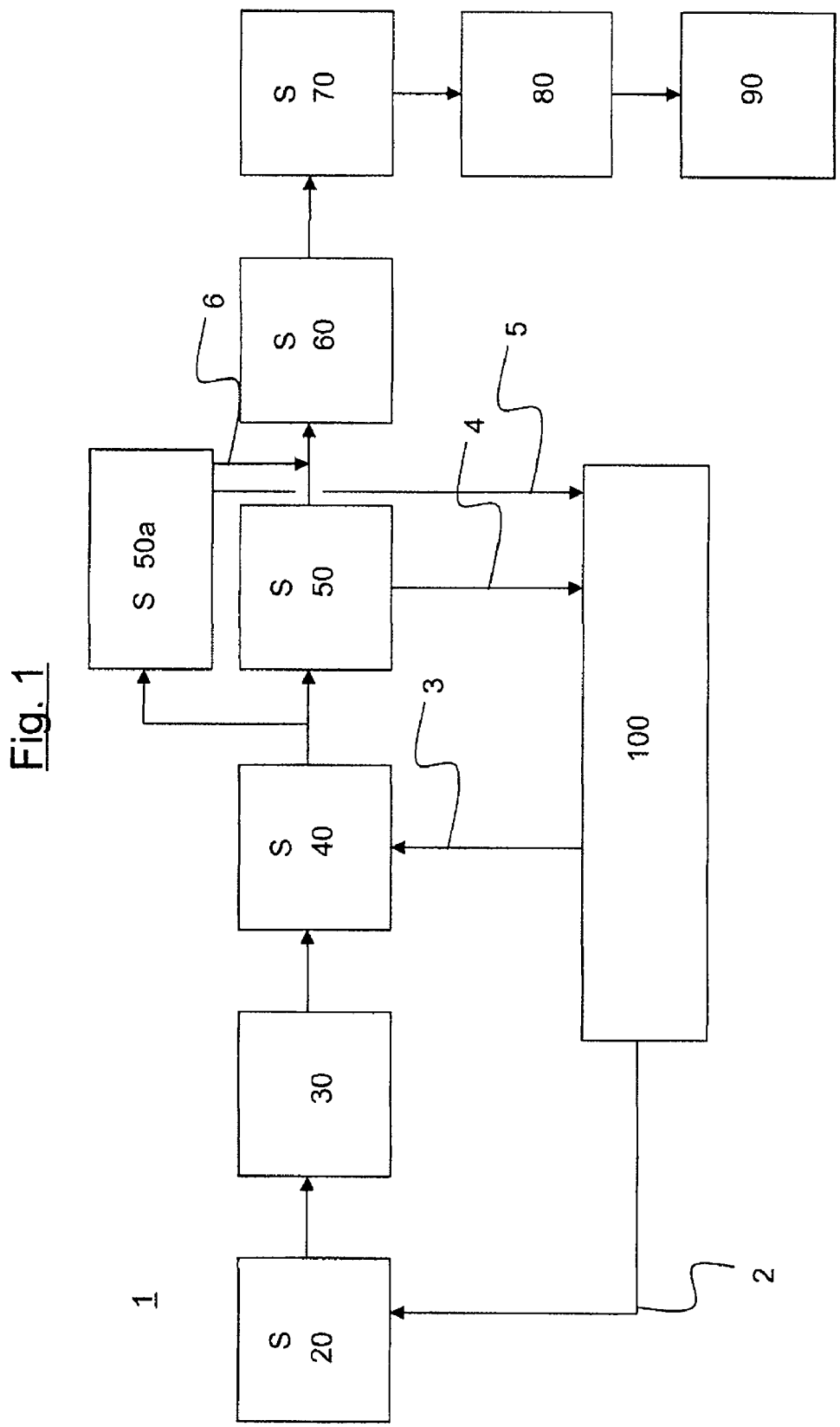

PROCESS FOR PREPARING CYANOHYDRINS AND THEIR USE IN THE PREPARATION OF ALKYL ESTERS OF METHACRYLIC ACID

The present invention relates to a process for preparing acetone cyanohydrin and to a process for preparing alkyl methacrylates, in which an acetone cyanohydrin as can be prepared in accordance with the present invention is used.

The preparation of alkyl methacrylates frequently comprises at least one process step in which acetone cyanohydrin serves as a starting material. Cyanohydrins are compounds which are frequently subject to thermal decomposition processes at elevated temperature. The main decomposition products formed in this case are frequently hydrocyanic acid and acetone again, but further by-products are also often detected.

The decomposition of cyanohydrins proceeds under suitable circumstances frequently at temperatures of more than about 70° C. The decomposition of cyanohydrins in reactions in which the cyanohydrin is an intermediate or a reactant for further reactions, for example in the preparation of alkyl methacrylates, has a direct effect in the form of a yield reduction in the overall reaction. For this reason, many publications known from the prior art have had for their object to at least substantially prevent a corresponding thermal decomposition of cyanohydrins in the course of their preparation.

US 2006/0111586 A1 relates to a process for minimizing the decomposition of cyanohydrins in the course of further processing in an exothermic reaction process in which cyanohydrins are reacted in a loop reactor having at least one reaction zone and a mixing apparatus, an amount of heat equivalent to the heat produced in the exothermic reaction being withdrawn from the reaction mixture. In further developments of the document, the formation of so-called "hotspots" in particular is suppressed by virtue of the proposal of an exceptionally complex addition sequence of the reactants. However, a problem in the process proposed is found to be that the measures presented entail a high degree of intelligent control capacity and can accordingly be exceptionally error-prone. In addition, there is no discussion of such problems in the preparation of cyanohydrins.

It was therefore an object of the present invention to provide a process for preparing acetone cyanohydrin, which can be used in an overall process for preparing alkyl methacrylates. It was a further object of the invention to provide a process for preparing acetone cyanohydrin, which allows very simple control of the reaction conditions and a very low level of control complexity. In addition, it was an object of the present invention to provide a process for preparing acetone cyanohydrin which as far as possible minimizes the thermal decomposition of the cyanohydrins in a simultaneously simple process.

These and further objects underlying the invention, as are apparent from the present text to the person skilled in the art with knowledge of the prior art, are achieved by processes as described in detail below.

SUMMARY OF THE INVENTION

The invention relates to a process for preparing acetone cyanohydrin, in which a reaction mixture comprising acetone and hydrocyanic acid is reacted in the presence of a catalyst in a loop reactor to form acetone cyanohydrin as the reaction product, the loop reactor having at least one apparatus for cooling the reaction mixture, at least one pump, at least one apparatus for mixing the reaction mixture and at least one feed orifice for feeding hydrocyanic acid, acetone and catalyst, the catalyst being fed in downstream of the feed of acetone or hydrocyanic acid or both.

The catalyst is fed in, for example, at a point in the loop reactor which is closer to an entry orifice of the reaction mixture into at least one apparatus for mixing the reaction mixture than to a feed orifice for feeding in hydrocyanic acid or a feed orifice for feeding in acetone or both feed orifices. At the same time, the catalyst can be fed in at a point in the loop reactor at which the path length of the reaction mixture before entry into an entry orifice into at least one apparatus for mixing the reaction mixture is at most 30% of the path length that the reaction mixture travels after the feeding of hydrocyanic acid and acetone before entry into an entry orifice into at least one apparatus for mixing the reaction mixture.

The residence time of the catalyst in the reaction mixture between feed and mixing in at least one apparatus for mixing the reaction mixture is, for example, at most about 10 s.

The catalyst can in principle be fed in continuously or intermittently. The temperature of the reaction mixture in the loop reactor is, for example, about 11 to about 70° C.

In a further embodiment of the invention, the catalyst used is an inorganic base or an organic base, for example an organic amine or a mixture of two or more organic amines.

Reaction product is preferably withdrawn continuously or intermittently from the loop reactor, the reaction product being cooled to a temperature of about 0 to about 10° C. in one or more heat exchangers after leaving the loop reactor, and, in a further embodiment of the invention, being admixed with an acid, especially with sulphuric acid. It has been found to be advantageous in some cases when sulphuric acid with a water content of 0.1 to 8% by weight is used.

In the process according to the invention, a sample of the reaction mixture can be withdrawn from the loop reactor, for example, at at least one point, in which case the sample is analyzed spectroscopically during or after the withdrawal. The sampling can be effected continuously or intermittently and the sample can be fed back to the loop reactor after the analysis.

The reaction is performed, for example, at a pH of about 6.5 to about 8.

The invention also relates to a process for preparing acetone cyanohydrin, in which a reaction mixture comprising acetone and hydrocyanic acid is reacted in the presence of a catalyst in a loop reactor to form acetone cyanohydrin as the reaction product, and in which the loop reactor has at least one apparatus for cooling the reaction mixture, at least one pump, at least one apparatus for mixing the reaction mixture and in each case at least one feed orifice for feeding hydrocyanic acid, acetone and catalyst, reaction product being withdrawn continuously or intermittently from the loop reactor, and the reaction product, after leaving the loop reactor, being cooled to a temperature of 0 to 10° C. in one or more heat exchangers and being admixed with sulphuric acid with a water content of 0.1 to 8% by weight. The catalyst is fed in, for example, downstream of the feed of acetone or hydrocyanic acid or both.

According to the invention, the catalyst can likewise be fed in at a point in the loop reactor which is closer to an entry orifice of the reaction mixture into at least one apparatus for mixing the reaction mixture than to a feed orifice for feeding in hydrocyanic acid or a feed orifice for feeding in acetone or both feed orifices, for example at a point in the loop reactor at which the path length of the reaction mixture before entry into an entry orifice of the reaction mixture into at least one apparatus for mixing the reaction mixture is at most 30% of the path length that the reaction mixture travels after the feeding of hydrocyanic acid and acetone before entry into an entry orifice of the reaction mixture into at least one apparatus for mixing the reaction mixture.

The residence time of the catalyst in the reaction mixture between feed and mixing in at least one apparatus for mixing the reaction mixture in this case too, in a preferred embodiment of the invention, is at most about 10 s.

The catalyst can be fed in continuously or intermittently; the temperature of the reaction mixture in the loop reactor is, for example, about 11 to about 70° C.; the catalyst used in the reaction may be an inorganic base or an organic base, for example an organic amine or a mixture of two or more organic amines.

According to the invention, a sample of the reaction mixture can be taken from the loop reactor at at least one point and the sample can be analysed spectroscopically. The sampling can be effected continuously or intermittently and the sample can be fed back to the loop reactor after the analysis. The reaction is performed, for example, at a pH of about 6.5 to about 8.

DETAILED DESCRIPTION OF THE INVENTION

According to the present invention, the reaction mixture of acetone and hydrocyanic acid is reacted in a loop reactor. It is equally possible and envisaged in accordance with the invention that, instead of a single loop reactor, a battery of two or more loop reactors, for example three, four or five loop reactors, can be used in the preparation process. The loop reactors may, for example, be arranged in series or in parallel.

A loop reactor usable in the context of the present invention has at least two feed orifices for feeding substances involved in the reaction or required for the reaction. The substances required in the reaction include, according to the present text, also those substances which are not necessarily spent in the course of the reaction but rather are necessary for the control of the reaction rates. These substances include, for example, catalysts.

The reaction is an exothermic reaction. In order to counteract decomposition of the acetone cyanohydrin formed in this reaction, the heat of reaction is typically removed by a suitable apparatus. The reaction can be conducted in principle as a batch process or as a continuous process; when a continuous process is preferred, the reaction is frequently performed in a loop reactor which is fitted out appropriately.

A main feature of a method leading to the desired product in high yields is often that the reaction product is cooled at sufficient reaction time and the reaction equilibrium is shifted in the direction of the reaction product. In addition, the reaction product is frequently admixed with an appropriate stabilizer to the advantage of the overall yield, in order to prevent decomposition in the course of the later workup to give the starting materials.

The mixing of the acetone and hydrocyanic acid reactants can in principle be effected in essentially any way. The method of mixing depends in particular on whether a batchwise mode, for example in a batch reactor, or a continuous mode, for example in a loop reactor, is selected.

In principle, it may be advantageous when the acetone is fed into the reaction via a reservoir vessel which has a scrubber tower. Venting lines which conduct waste air containing acetone and hydrocyanic acid can thus be conducted, for example, through this reservoir vessel. In the scrubbing tower which is attached to the reservoir vessel, the waste air escaping from the reservoir vessel can be scrubbed with acetone, which removes hydrocyanic acid from the waste air and recycles it into the process. For this purpose, for example, some of the amount of acetone introduced from the reservoir vessel into the reaction is conducted in the part-stream through a cooler, preferably through a brine cooler, into the top of the scrubbing tower and the desired result is thus achieved.

Depending on the size of the amount of end products to be produced, it may be advantageous to feed the acetone to the reaction from more than just one reservoir vessel. In this context, it is possible for each of the two or more reservoir vessels to bear a corresponding scrubbing tower. However, it is in many cases sufficient when only one of the reservoir vessels is equipped with a corresponding scrubbing tower. In this case, it is, however, often advisable for corresponding lines which conduct waste air and can transport acetone and hydrocyanic acid to be conducted through this vessel or through this scrubbing tower.

The temperature of the acetone in the reservoir may in principle be within an essentially arbitrary range, provided that the acetone is in the liquid state at the appropriate temperature. The temperature in the reservoir vessel is advantageously, however, about 0 to about 20° C.

In the scrubbing tower, the acetone used for scrubbing is cooled by means of an appropriate cooler, for example by means of a plate cooler, with brine to a temperature of about 0 to about 10° C. The temperature of the acetone on entry into the scrubbing tower is therefore preferably, for example, about 2 to about 6° C.

The hydrocyanic acid required in the reaction can be introduced into the reactor either in liquid or in gaseous form. It may, for example, be crude gas from the BMA process or from the Andrussow process.

The hydrogen cyanide can, for example, be liquefied, for example by the use of an appropriate cooling brine. Instead of liquefied hydrocyanic acid, coking oven gas can be used. For example, hydrogen cyanide-containing coking oven gases, after scrubbing with potash, are scrubbed continuously in countercurrent with acetone which contains 10% water, and the reaction to give acetone cyanohydrin can be carried out in the presence of a basic catalyst in two gas scrubbing columns connected in series.

In a further embodiment, a gas mixture comprising hydrogen cyanide and inert gases, especially a crude gas from the BMA process or from the Andrussow process, can be reacted with acetone in the presence of a basic catalyst and acetone cyanohydrin in a gas-liquid reactor.

In the process described here, preference is given to using a BMA crude gas or an Andrussow crude gas. The gas mixture resulting from the abovementioned customary processes for preparing hydrogen cyanide can be used as such or after an acid scrubbing. The crude gas from the BMA process, in which essentially hydrocyanic acid and hydrogen are formed from methane and ammonia, contains typically 22.9% by volume of HCN, 71.8% by volume of $H_2$, 2.5% by volume of $NH_3$, 1.1% by volume of $N_2$, 1.7% by volume of $CH_4$. In the known Andrussow process, hydrocyanic acid and water are formed from methane and ammonia and atmospheric oxygen. The crude gas of the Andrussow process, when oxygen is used as the oxygen source, contains typically 8% by volume of HCN, 22% by volume of $H_2$, 46.5% by volume of $N_2$, 15% by volume of $H_2O$, 5% by volume of CO, 2.5% by volume of $NH_3$ and 0.5% by volume each of $CH_4$ and $CO_2$.

When a non-acid-scrubbed crude gas from the BMA process or Andrussow process is used, the ammonia present in the crude gas frequently acts as a catalyst for the reaction. Since the ammonia present in the crude gas frequently exceeds the amount required as a catalyst and can therefore lead to high losses of sulphuric acid used for stabilization, such a crude gas is often subjected to an acid scrubbing in order to eliminate ammonia therefrom. When such an acid-scrubbed crude gas is used, it is then necessary, however, to add a suitable basic catalyst to the reactor in a catalytic amount. In principle, known inorganic or organic basic compounds may function as the catalyst.

Hydrogen cyanide in gaseous or in liquid form, or a gas mixture comprising hydrogen cyanide, and acetone are fed continually to a loop reactor in the continuous mode. In this case, the loop reactor comprises at least one means of feeding acetone or two or more such means, at least one means for feeding liquid or gaseous hydrocyanic acid, or two or more such means, and at least one means for feeding a catalyst.

A loop reactor useable in the process element described further comprises at least one pump, or two or more pumps, and at least one mixing apparatus for mixing the reaction mixture, or two or more such mixing apparatuses. Suitable pumps are in principle all pumps which are suitable for ensuring the circulation of the reaction mixture in the loop reactor.

The catalyst is added in the loop reactor preferably downstream of the pump and upstream of a mixing element present in the loop reactor. In the reaction described, catalysts are used, for example, in such an amount that the overall reaction is conducted at a pH of not more than 8, in particular not more than about 7.5 or about 7. It may be preferred when the pH in the reaction varies within a range of about 6.5 to about 7.5, for example about 6.8 to about 7.2.

Alternatively to the addition of the catalyst into the loop reactor downstream of the pump and upstream of a mixing apparatus, it is also possible in the process described to feed the catalyst into the loop reactor together with the acetone. In such a case, it may be advantageous when appropriate mixing of acetone and catalyst is ensured before feeding into the loop reactor. Appropriate mixing can be effected, for example, by the use of a mixer with moving parts or by use of a static mixer.

When a continuous process in a loop reactor is selected as the operating mode in the process described, it may be appropriate to examine the state of the reaction mixture by instantaneous or continual analyses. This offers the advantage that, where appropriate, it is also possible to react rapidly to changes in state in the reaction mixture. Furthermore, it is thus possible, for example, to meter in the reactants very precisely in order to minimize yield losses.

Corresponding analysis can be effected, for example, by sampling in the reactor loop. Suitable analysis methods are, for example, pH measurement, measurement of the exothermicity or measurement of the composition of the reaction mixture by suitable spectroscopic processes.

Especially within the context of conversion monitoring, quality aspects and safety, it has been found to be useful to determine the conversion in the reaction mixture via the heat removed from the reaction mixture and to compare it with the heat which is released theoretically.

In the case of suitable selection of the loop reactor, the actual reaction can in principle be effected within the tube systems arranged within the loop reactor.

Since the reaction, however, is exothermic, in order to avoid yield loss, sufficient cooling and sufficient removal of the heat of reaction should be ensured. It has frequently been found to be advantageous when the reaction proceeds within a heat exchanger, preferably within a tube bundle heat exchanger. Depending on the amount of product to be produced, the capacity of an appropriate heat exchanger can be selected differently. For industrial scale processes, heat exchangers having a volume of about 10 to about 40 $m^3$ in particular have been found to be particularly suitable. The tube bundle heat exchangers used with preference are heat exchangers which have a tube bundle flowed through by liquid within a jacket flowed through by liquid. Depending on the tube diameter, packing density, etc., the heat transfer between the two liquids can be adjusted appropriately. It is possible in principle in the process described to conduct the reaction to the effect that the reaction mixture is conducted through the heat exchanger in the tube bundle itself and the reaction takes place within the tube bundle, the heat being removed from the tube bundle into the jacket liquid.

However, it has likewise been found to be practicable and in many cases to be viable to conduct the reaction mixture through the jacket of the heat exchanger, while the liquid used for cooling is circulated within the tube bundle. It has in many cases been found to be advantageous when the reaction mixture is distributed within the jacket by means of flow resistances, preferably deflecting plates, to achieve a higher residence time and better mixing.

The ratio of jacket volume to the volume of the tube bundle may, depending on the design of the reactor, be about 10:1 to about 1:10; the volume of the jacket is preferably greater than the volume of the tube bundle (based on the contents of the tubes).

The heat removal from the reactor is adjusted with an appropriate coolant, for example with water, such that the reaction temperature is within a corridor of about 25 to about 45° C., in particular about 30 to about 38° C., in particular about 33 to about 35° C.

A product is removed continuously from the loop reactor. The product has a temperature within the abovementioned reaction temperatures, for example a temperature of about 35° C. The product is cooled by means of one or more heat exchangers, especially by means of one or more plate heat exchangers. For example, brine cooling is used. The temperature of the product after cooling should be about 0 to 10° C., in particular 1 to about 5° C. The product is preferably transferred into a storage vessel which has a buffer function. In addition, the product in the storage vessel can be cooled further, for example, by constantly removing a part-stream from the storage vessel to a suitable heat exchanger, for example to a plate heat exchanger, or kept at a suitable storage temperature. It is entirely possible that continued reaction can take place in the storage vessel.

The product can be recycled into the storage vessel in any way in principle. However, it has been found to be advantageous in some cases that the product is recycled by means of a system composed of one or more nozzles into the storage vessel such that corresponding mixing of the stored product takes place within the storage vessel.

Product is also removed continuously from the storage vessel into a stabilization vessel. The product is admixed there with a suitable acid, for example with $H_2SO_4$. This deactivates the catalyst.

A loop reactor usable in the context of the present invention contains a reaction mixture in the operating state and has at least one apparatus for mixing the reaction mixture. The apparatus is arranged such that it is passed through at least once by the reaction mixture present in the loop reactor during one pass of the loop reactor. Suitable mixing apparatuses are both mixing apparatuses with mobile elements and so-called static mixers in which immobile flow resistances are provided. Suitable mixing apparatus is, for example, static mixers, simple plates provided with orifices, Venturi apparatus, nozzle mixers, stirred apparatus, other mixing apparatus, spray nozzles and the like, provided that they can be used successfully in a loop mixer for the mixing of the reactants. A corresponding mixing apparatus can perform the mixing operation, for example, with the aid of external energy supply.

However, it is equally possible and preferred in the context of the present invention, in a further embodiment, when the reactants are mixed exclusively by the kinetic energy present in the reaction mixture in the loop reactor. The kinetic energy present in this way can viably be utilized, for example, by means of static mixers. In the case of use of static mixers, suitable examples are those which allow an operational elevated pressure of at least about 10 bar, for example at least about 15 bar or at least about 20 bar under operating conditions without significant restrictions in the functioning. Appropriate mixers may consist of plastic or metal. Suitable plastics are, for example, PVC, PP; HDPE, PVDF, PVA or PTFE. Metal mixers may consist, for example, of nickel alloys, zirconium, titanium and the like. Likewise suitable are, for example, rectangular mixers.

According to the invention, the reaction of hydrocyanic acid and acetone to give acetone cyanohydrin proceeds in the presence of a catalyst. Suitable catalysts are in principle basic compounds, for example inorganic basic compounds or organic basic compounds. Suitable examples are any alkaline compounds, such as ammonia, sodium hydroxide solution or potassium hydroxide solution, which can catalyse the reaction of acetone and hydrocyanic acid to give acetone cyanohydrin. The suitable inorganic basic compounds include, for example, metal oxides or metal hydroxides, especially the hydroxides of the alkali metals or alkoxides of the alkali metals, alkali metals in the context of the present text being understood to mean lithium, sodium and potassium. Performance of the process according to the invention with corresponding compounds of rubidium and caesium is certainly possible, but will usually be avoided for economic reasons.

In a further embodiment of the present invention which is preferred in many cases, the process according to the invention will be performed using organic bases. Suitable organic bases are in principle all organic compounds which do not have an adverse influence on the inventive reaction and additionally, when the cyanohydrin prepared in accordance with the invention is to be used in an integrated process leading further, for example in a process for preparing alkyl methacrylates, can either be removed easily from the reaction mixture or, when it remains in the reaction mixture, does not have an adverse influence on the stages leading further.

In a further embodiment of the present invention, particular preference is given to amines as organic bases. It has been found to be advantageous when the catalyst used is an organic catalyst, especially an amine. Suitable examples are secondary or tertiary amines, such as diethylamine, dipropylamine, triethylamine, tri-n-propylamine and the like.

It has been found to be advantageous in accordance with the present invention when the individual substances involved in the reaction are added such that the reactants are mixed particularly intimately with a catalyst which promotes the reaction, such that, when the need exists to add a catalyst at a certain time, the catalyst is fed to the reaction mixture such that very good mixing of the compounds to be reacted with one another has already taken place; on the other hand, the mixing between catalyst and the reactants likewise takes place very rapidly and very thoroughly, such that a minimum time lapses until complete or largely complete homogenization.

For this purpose, it has been found to be advantageous in accordance with the invention when certain relations exist between the addition points for the reactants, i.e. acetone and hydrocyanic acid, the addition point of the catalyst and the mixing apparatus in the loop reactor. For example, it may be advantageous in accordance with the invention when the addition site or the addition point of the two reactants, acetone and hydrocyanic acid, are comparatively close to one another. For example, the addition site for the acetone may be separated from the addition site for the hydrocyanic acid by a distance which is less than 20% of the total length of the loop reactor, in particular less than 10% of the total length of the loop reactor.

This arrangement has an advantageous effect in that, after the addition of the reactants, mixing of the reactants can take place very rapidly, but without the reaction already proceeding sufficiently rapidly owing to a high catalyst concentration that the formation of local overheating zones would be expected. It has also been found to be advantageous in accordance with the invention when the distance from the addition site for acetone or from the addition site for hydrocyanic acid to the apparatus for mixing the reactants in the loop reactor, which is preferably a static mixing apparatus, is selected such that it is about 50% to about 75% of the total length of the loop reactor.

It has additionally been found to be advantageous in some cases in the context of the present invention when the addition point for the catalyst is selected such that the distance between addition point of the catalyst and the apparatus for mixing the reaction mixture in the loop reactor is at most 50% of the distance which is between the addition point for acetone or the addition point for hydrocyanic acid, depending on which of these addition points is closer to the apparatus for mixing the reaction mixture in the loop reactor. In further preferred embodiments of the present invention, the distance between addition point and apparatus for mixing the reaction mixture in the loop reactor of the catalyst in relation to the addition point of the acetone or of hydrocyanic acid, depending on which of the two addition points is closer to the apparatus for mixing the reaction mixture in the loop reactor, is at most about 30% or at most about 20% or at most about 10% or at most about 5%.

The above-described arrangement of the addition points for the reactants and other reaction assistants, especially for the catalyst, has a number of advantages regarding the stability of the reaction in the loop reactor. The selection of the addition point for acetone and hydrocyanic acid at a distance from the apparatus for mixing the reaction mixture in the loop reactor and especially at a distance from the addition point for the catalyst is advantageous to the effect that, before contacting of the catalyst with the reaction mixture, mixing of the reactants can already take place to such an extent that an already largely homogeneous mixture meets the catalyst. This largely prevents local concentration maxima, which ensures a more uniform reaction and hence results in a yield increase owing to a smaller loss of acetone cyanohydrin as a result of dissociation. The arrangement of the addition point for the catalyst in the immediate proximity of the apparatus for the mixing of the reaction mixture additionally ensures rapid homogenization of the reaction mixture with the added catalyst. In this context too, it has been found that the significantly improved homogenization and the rapid homogenization reduce the formation of local concentration gradients and can thus increase the yield.

In a further embodiment of the present invention, it has additionally been found to be advantageous when the loop reactor has at least one pump within the reactor loop. In a further embodiment of the present invention, the pump is integrated into the loop reactor such that it is arranged between the addition point for the acetone and hydrocyanic acid reactants and the addition point of the catalyst.

The reaction mixture is cooled in the reactor in such a way that the reaction mixture has an essentially uniform temperature during the operation of the loop reactor. The temperature variations are preferably less than about 20° C., for example less than about 10° C. or less than about 5° C.

Preferably at least one heat exchanger is arranged in the loop reactor such that the reaction mixture, in the course of operation, can pass through the heat exchanger at least once per pass of the loop reactor. If appropriate, it is also possible for two or three heat exchangers in series or in parallel to cool the reaction mixture. The cooling is effected preferably by means of water, but any other coolant is also suitable in principle in the context of the present invention. The temperature in the reaction mixture is adjusted to a temperature between 10 and about 60° C., in particular to a temperature of about 30 to about 40° C., as described in the present text.

The reaction mixture can be withdrawn from the loop reactor continuously or intermittently, but preferably continuously. A reaction mixture withdrawn from the loop reactor has a temperature which should advantageously be lowered further. To this end, in the context of the present invention, in a further embodiment of the subject matter of the invention, the reaction mixture removed is cooled by means of a further heat exchanger, preferably by means of a plate heat exchanger, to a temperature of less than 10° C., preferably to a temperature of about 0 to about 5° C.

Subsequently, the mixture is transferred to the above-described storage vessel in which, for example, a postreaction can take place. The vessel is preferably circulated such that a portion of the contents is constantly withdrawn from the vessel, cooled by means of a further heat exchanger to the temperature predefined for the vessel, for example about 0 to about 5° C., and then returned into the vessel. The recycling into the vessel and especially the feeding into the mixture already present in the vessel, in a further embodiment of the present invention, are preferably selected such that the stream of the recycled material ensures mixing of the reaction product present in the vessel. For example, such a recycling of the mixture withdrawn into the vessel can be effected by means of an appropriately suitable nozzle.

Subsequently, the material present in the vessel, either intermittently or continuously, is transferred into a further vessel in which a stabilization of the product takes place. In a further embodiment of the present invention, the stabilization is effected with an acid, especially with a mineral acid. A suitable example is sulphuric acid having a water content of about 0.1 to about 10%, for example about 0.5 to about 8% or about 1 to about 6%. The amount of acid added depends on the pH to be established in the mixture. It has been found to be very particularly suitable when the pH is adjusted to a value of about 1 to about 4, in particular about 1.5 to about 2.5, for example 2.

The crude acetone cyanohydrin as the reaction product is subsequently subjected to a purification. A purification by means of a column, especially by means of a rectification column having about 10 to about 18 column trays, has been found to be suitable in many cases. The crude acetone cyanohydrin can be added to the rectification column, for instance, in the upper third of the column. The temperature of the acetone cyanohydrin may in principle be about 0 to about 100° C. It has in various cases been found to be favourable when a preheating of the product takes place. Advantageously, the product is preheated, for example, by means of heat exchange with the purified acetone cyanohydrin drawn off from the rectification column. In the case of such a heat exchange, for example, acetone cyanohydrin with a temperature of about 100° C. is withdrawn from the column bottom and, in a heat exchange, cooled with the acetone cyanohydrin to be purified to a temperature of about 60 to about 80° C., the heat transfer being adjusted such that the acetone cyanohydrin to be introduced into the column is brought to about the same temperature.

A further subject of the invention consists in a process for preparing acetone cyanohydrin, in which a reaction mixture comprising acetone and hydrocyanic acid is reacted in the presence of a catalyst in a loop reactor to form acetone cyanohydrin as the reaction product, and in which the loop reactor has at least one apparatus for cooling the reaction mixture, at least one pump, at least one apparatus for mixing the reaction mixture and in each case at least one feed orifice for feeding hydrocyanic acid, acetone and catalyst, reaction product being withdrawn continuously or intermittently from the loop reactor, and the reaction product, after leaving the loop reactor, being cooled to a temperature of 0 to 10° C. in one or more heat exchangers and being admixed with sulphuric acid with a water content of 0.1 to 8% by weight.

It has been found in accordance with the invention that treatment of a reaction product as obtained in accordance with the present invention with sulphuric acid having a water content of 0.1 to 8% by weight, for example having a water content of about 0.5 to about 7% by weight, or about 1 to about 6% by weight or about 2 to about 5% by weight or about 3 to about 4.5% by weight, for example 4% by weight, allows excellent stabilization to be achieved. In addition, such a treatment is suitable as a preparation for use in processes leading further, especially as a preparation for use in an integrated process for preparing alkyl methacrylates, in which, as a next step, for example, the acetone cyanohydrin is amidated.

The measures proposed in the context of the present invention are suitable both individually and separately for improving the yield in the processes for preparing acetone cyanohydrin. The measures can be employed in any combination; the teaching of the present text explicitly also encompasses such combinations.

The process according to the invention has a series of advantages, especially with regard to the fact that it is particularly suitable for incorporation into a process for preparing alkyl methacrylates. The present process leads to particularly pure products in high yield. The present invention therefore also provides a process for preparing alkyl methacrylates, which uses acetone cyanohydrin, as can be obtained in accordance with the present invention, in at least one step.

Various process elements will be illustrated hereinafter, which can in principle be combined with the present invention individually or as an ensemble of two or more of the process elements mentioned. In some cases, it may be advantageous when the process elements presented in the present text are combined with the present invention in such a way that they are combined overall to give a process for preparing esters of methacrylic acid or a process for preparing methacrylic acid. However, it should also be pointed out that advantageous effects can also be achieved when the subject matter of the present invention is used as such in another environment or is combined only with some of the process elements presented here.

ACH Workup

In a further process element which can be used in connection with the present invention, acetone cyanohydrin which has been obtained in a preceding stage, for example from the reaction of acetone with hydrocyanic acid, is subjected to a distillative workup. The stabilized crude acetone cyanohydrin is freed of low-boiling constituents by means of a corresponding column. A suitable distillation process can be conducted, for example, by means of only one column. However, it is likewise possible, in an appropriate purification of crude acetone cyanohydrin, to use a combination of two or more distillation columns, also combined with a falling-film evaporator. In addition, two or more falling-film evaporators or else two or more distillation columns may be combined with one another.

The crude acetone cyanohydrin comes from the storage to the distillation generally with a temperature of about 0 to about 15° C., for example a temperature of about 5 to about 10° C. In principle, the crude acetone cyanohydrin can be introduced directly into the column. However, it has been found to be useful in some cases when the crude cool acetone cyanohydrin, by means of a heat exchanger, first takes up some of the heat of the product already purified by distillation. Therefore, in a further embodiment of the process described here, the crude acetone cyanohydrin is heated by means of a heat exchanger to a temperature of about 60 to 80° C.

The acetone cyanohydrin is purified by distillation by means of a distillation column having more than 10 trays, or by means of a battery of two or more corresponding suitable distillation columns. The column bottom is heated preferably with steam. It has been found to be advantageous when the bottom temperature does not exceed a temperature of 140° C.; good yields and good purification have been achieved when the bottom temperature is not greater than about 130° C. or not higher than about 110° C. The temperature data are based on the wall temperature of the column bottom.

The crude acetone cyanohydrin is fed to the column body in the upper third of the column. The distillation is performed preferably under reduced pressure, preferably at a pressure of about 50 to about 900 mbar, in particular about 50 to about 250 mbar and with good results between 50 and about 150 mbar.

At the top of the column, gaseous impurities, especially acetone and hydrocyanic acid, are removed, the removed gaseous substances are cooled by means of one heat exchanger or a battery of two or more heat exchangers. Preference is given here to using brine cooling with a temperature of about 0 to about 10° C. This gives the gaseous constituents of the vapours the opportunity to condense. The first condensation stage may take place, for example, at standard pressure. However, it is equally possible and has been found to be advantageous in some cases when this first condensation stage is effected under reduced pressure, preferably at the pressure which prevails in the distillation. The condensate is passed on into a cooled collecting vessel and collected there at a temperature of about 0 to about 15° C., in particular at about 5 to about 10° C.

The gaseous compounds which do not condense in the first condensation step are removed from the reduced pressure chamber by means of a vacuum pump. In principle, any vacuum pump can be used here. However, it has been found to be advantageous in many cases to use a vacuum pump which, owing to its design, does not lead to the introduction of liquid impurities into the gas stream. Preference is therefore given here, for example, to using dry-running vacuum pumps.

The gas stream which escapes on the pressure side of the pump is conducted through a further heat exchanger which is preferably cooled with brine at a temperature of about 0 to about 15° C. Constituents which condense here are likewise collected in the collecting vessel which already collects the condensates obtained under vacuum conditions. The condensation performed on the pressure side of the vacuum pump can be effected, for example, by a heat exchanger, but also with a battery of two or more heat exchangers arranged in series or in parallel. Gaseous substances remaining after this condensation step are removed and sent to any further utilization, for example a thermal utilization.

The collected concentrates may likewise be utilized further as desired. However, for economic reasons, it has been found to be extremely advantageous to recycle the condensates into the reaction for preparing acetone cyanohydrin. This is effected preferably at one or more points which enable access to the loop reactor. The condensates may in principle have any composition provided that they do not disrupt the preparation of the acetone cyanohydrin. In many cases, a predominant amount of the condensate will, however, consist of acetone and hydrocyanic acid, for example in a molar ratio of about 2:1 to about 1:2, frequently in a ratio of about 1:1.

The acetone cyanohydrin obtained from the bottom of the distillation column is first cooled to a temperature of about 40 to about 80° C. by the cold crude acetone cyanohydrin fed in by means of a first heat exchanger. Subsequently, the acetone cyanohydrin is cooled to a temperature of about 30 to about 35° C. by means of at least one further heat exchanger and optionally stored intermediately.

Amidation

In a further process element as frequently provided in the preparation of methacrylic acid or of esters of methacrylic acid, acetone cyanohydrin is subjected to a hydrolysis. At different temperature levels after a series of reactions, this forms methacrylamide as the product.

The reaction is brought about in a manner known to those skilled in the art by a reaction between concentrated sulphuric acid and acetone cyanohydrin. The reaction is exothermic, which means that heat of reaction is advantageously removed from the system.

The reaction here too can again be performed in a batchwise process or in continuous processes. The latter has been found to be advantageous in many cases.

When the reaction is performed in a continuous process, the use of loop reactors has been found to be useful. The reaction can be effected, for example, in only one loop reactor. However, it may be advantageous when the reaction is performed in a battery of two or more loop reactors.

In the process described, a suitable loop reactor has one or more feed points for acetone cyanohydrin, one or more feed points for concentrated sulphuric acid, one or more gas separators, one or more heat exchangers and one or more mixers.

The hydrolysis of acetone cyanohydrin with sulphuric acid to give methacrylamide is, as already described, exothermic. The heat of reaction which arises in the reaction must, however, at least largely be withdrawn from the system, since the yield falls with increasing temperature in the reaction. It is possible in principle to achieve a rapid and comprehensive removal of the heat of reaction with appropriate heat exchangers. However, it may also be disadvantageous to cool the mixture too greatly, since a sufficient heat transfer is required for appropriate exchange at the heat exchangers. Since the viscosity of the mixture rises greatly with falling temperature, the circulation in the loop reactor is firstly complicated, and sufficient removal of the reaction energy from the system can secondly no longer be ensured.

In addition, excessively low temperatures in the reaction mixture can lead to a crystallization of constituents of the reaction mixture at the heat exchangers. This further worsens the heat transfer, as a result of which a clear yield reduction can be detected. In addition, the loop reactor cannot be charged with the optimal amounts of reactants, such that the efficiency of the process suffers overall.

In one embodiment of the process, a portion, preferably about two thirds to about three quarters, of the volume flow rate from a stream of acetone cyanohydrin is introduced into a first loop reactor. A first loop reactor preferably has one or more heat exchangers, one or more pumps, one or more mixing elements and one or more gas separators. The circulation streams which pass through the first loop reactor are preferably in the range of about 100 to 450 m$^3$/h, preferably in a range of 200 to 400 m$^3$/h and more preferably in a range of about 250 to 350 m$^3$/h. In an at least one further loop reactor which follows the first loop reactor, the circulation streams are preferably in a range of about 40 to 450 m$^3$/h, preferably in a range of 50 to 400 m$^3$/h and more preferably in a range of about 60 to 350 m$^3$/h. Moreover, a preferred temperature difference over the heat exchangers is about 1 to 10° C., particular preference being given to about 2 to 7° C.

The acetone cyanohydrin can in principle be fed into the loop reactor at any point. However, it has been found to be advantageous when the feed is into a mixing element, for example into a mixer with moving parts or a static mixer. The sulphuric acid is advantageously fed in upstream of the acetone cyanohydrin addition. Otherwise, it is, however, likewise possible to feed the sulphuric acid into the loop reactor at any point.

The ratio of the reactants in the loop reactor is controlled such that an excess of sulphuric acid is present. The excess of sulphuric acid is, based on the molar ratio of the constituents, about 1.8:1 to about 3:1 in the first loop reactor and about 1.3:1 to about 2:1 in the last loop reactor.

In some cases, it has been found to be advantageous to perform the reaction in the loop reactor with such an excess of sulphuric acid. The sulphuric acid may serve here, for example, as a solvent and keep the viscosity of the reaction mixture low, which can ensure a higher removal of heat of reaction and a lower temperature of the reaction mixture. This can entail significant yield advantages. The temperature in the reaction mixture is about 90 to about 120° C.

The heat removal is ensured by one or more heat exchangers in the loop reactor. It has been found to be advantageous when the heat exchangers have a suitable sensor system for controlling the cooling performance in order to prevent excessively great cooling of the reaction mixture for the aforementioned reasons. For example, it may be advantageous to measure the heat transfer in the heat exchanger or in the heat exchangers point by point or continuously and to adjust the cooling performance of the heat exchangers thereto. This can be done, for example, via the coolant itself. It is equally possible to achieve appropriate heating of the reaction mixture by corresponding variation of the addition of the reactants and by the generation of more heat of reaction. A combination of the two possibilities is also conceivable. The loop reactor should additionally have at least one gas separator. One method is to withdraw product formed continuously from the loop reactor via the gas separator. Another method is thus to withdraw the gases formed in the reaction from the reaction chamber. The gas formed is mainly carbon monoxide. The product withdrawn from the loop reactor is preferably transferred into a second loop reactor. In this second loop reactor, the reaction mixture comprising sulphuric acid and methacrylamide, as has been obtained by the reaction in the first loop reactor, is reacted with the remaining part-stream of acetone cyanohydrin. In this case, the excess of sulphuric acid from the first loop reactor, or at least some of the excess sulphuric acid, reacts with the acetone cyanohydrin to form further methacrylamide. The performance of the reaction in two or more loop reactors has the advantage that, owing to the sulphuric acid excess in the first loop reactor, the pumpability of the reaction mixture and hence the heat transfer and ultimately the yield are improved. In turn, at least one mixing element, at least one heat exchanger and at least one gas separator are arranged in the second loop reactor. The reaction temperature in the second loop reactor is likewise about 90 to about 120° C.

The problem of the pumpability of the reaction mixture, of heat transfer and of a minimum reaction temperature occurs in every further loop reactor just as it does in the first. Therefore, the second loop reactor too advantageously has a heat exchanger whose cooling performance can be controlled by an appropriate sensor system.

The acetone cyanohydrin is again fed in in a suitable mixing element, preferably into a static mixer.

The product is withdrawn from the gas separator of the second loop reactor and heated to a temperature of about 140 to about 180° C. to complete the reaction and to form the methacrylamide.

The heating is preferably performed such that the maximum temperature is attained only for a minimum period, for example for a time of about one minute to about 30 minutes, in particular for a time of about two to about eight or about three to about five minutes. This can in principle be effected in any apparatus for achieving such a temperature for such a short period. For example, the energy can be supplied in a conventional manner by electrical energy or by steam. However, it is equally possible to supply the energy by means of electromagnetic radiation, for example by means of microwaves.

In various cases, it has been found to be advantageous when the heating step is effected in a heat exchanger with two-stage or multistage arrangement of tube coils which may preferably be present in an at least double, opposite arrangement. This heats the reaction mixture rapidly to a temperature of about 140 to 180° C.

The heat exchanger can be combined, for example, with one or more gas separators. For example, it is possible to conduct the reaction mixture through a gas separator after it leaves the first tube coil in the heat exchanger. This can remove, for example, gaseous components formed during the reaction from the reaction mixture. It is equally possible to treat the reaction mixture with a gas separator after it leaves the second coil. It may additionally be found to be advantageous to treat the reaction mixture with a gas separator both after it leaves the first tube coil and after it leaves the second tube coil.

The amide solution thus obtainable generally has a temperature of more than 100° C., typically a temperature of about 140 to 180° C.

The gaseous compounds obtained in the amidation can in principle be disposed of in any way or sent to further processing. However, it may be advantageous in some cases when the appropriate gases are combined in a transport line in such a way that they are optionally pressurized either continuously or as required, for example with steam pressure, and can thus be transported further.

Esterification

A further step which constitutes a process element and can be used in the present invention in connection with the process according to the invention is a hydrolysis of methacrylamide to methacrylic acid and its subsequent esterification to methacrylic esters. This reaction can be performed in one or more heated, for example steam-heated, tanks. However, it has in many cases been found to be advantageous when the esterification is performed in at least two successive tanks, but, for example, also in three or four or more successive tanks. In this case, a solution of methacrylamide is introduced into the tank or into the first tank of a battery of tanks comprising two or more tanks.

It is frequently preferred to perform a corresponding esterification reaction with a battery of two or more tanks. Reference will therefore be made hereinafter exclusively to this variant.

In the process described here, it is possible, for example, to feed an amide solution as obtainable from the amidation reaction described here into a first tank. The tank is heated, for example, with steam. The amide solution supplied generally has an elevated temperature, for example a temperature of about 100 to about 180° C., essentially corresponding to the exit temperature of the amide solution from the amidation reaction presented above. An alkanol is also fed to the tanks, which can be used for the esterification.

Suitable alkanols here are in principle any alkanols having 1 to about 4 carbon atoms, which may be linear or branched, saturated or unsaturated, particular preference being given to methanol. These alkanols may likewise be used together with methacrylic esters, which is the case especially in transesterifications.

The tank is also charged with water, so that there is a total water concentration in the tank of about 13 to about 26% by weight, in particular about 18 to about 20% by weight.

The amount of amide solution and of alkanol is controlled such that a total molar ratio of amide to alkanol of about 1:1.4 to about 1:1.6 exists. The alkanol can be distributed over the tank battery such that the molar ratio in the first reactor is about 1:1.1 to about 1:1.4 and, in the subsequent reaction stages, based on the total amide stream, molar ratios of about 1:0.05 to about 1:0.3 are established. The alkanol fed into the esterification may be composed of "fresh alkanol" and alkanol from recycling streams of the workup stages and, if required, also of recycling streams of the downstream processes of the production system.

The first tank can be charged with water in principle such that water is fed to the tank from any source, provided that this water has no ingredients which might adversely affect the esterification reaction or the downstream process stages. For example, demineralized water or spring water can be fed to the tank. However, it is likewise possible to feed a mixture of water and organic compounds to the tank, as obtained, for example, in the purification of methacrylic acid or methacrylic esters. In a preferred embodiment of the process presented here, the tank is charged at least partly with a mixture of water and such organic compounds.

When a battery of two or more tanks is used in the esterification reaction, the gaseous substances formed, especially the methacrylic esters, can in principle be drawn off individually from each tank and fed to a purification. However, it has been found in some cases to be advantageous when, in a battery of two or more tanks, the gaseous products from the first tank are first fed into the second reaction vessel without the gaseous compounds from the first tank being fed directly to a purification. This procedure offers the advantage that the frequently high evolution of foam in the first tank need not be counteracted by complicated defoaming apparatus. In the case of passage of the gaseous substances from the first tank into the second tank, the foam which has been formed in the first tank and may have been entrained also enters the reaction chamber of the second tank in a simple manner. Since the foam formation there is generally significantly lower, there is no need to use defoaming apparatus.

The second tank arranged downstream of a first tank then firstly takes up the overflow of the first tank; secondly, it is fed with the gaseous substances formed in the first tank or which are present in the first tank. The second tank and any following tanks are likewise charged with methanol. It is preferred here that the amount of methanol decreases by at least 10% from tank to tank, based in each case on the preceding tank. The water concentration in the second tank and in the further tanks may differ from that of the first tank; the concentration differences are, though, often small.

The vapours formed in the second tank are removed from the tank and introduced into the bottom of a distillation column.

When the esterification is performed with a battery of three or more tanks, the overflow of the second tank is transferred in each case into a third tank, and the overflow of the third tank, if appropriate, into a fourth tank. The further tanks are likewise steam-heated. The temperature in tanks 3 and, if appropriate, 4 is preferably adjusted to about 120 to about 140° C.

The vapours escaping from the tanks are passed into a distillation column, this preferably being effected in the lower region of the distillation column. The vapours comprise an azeotropic mixture of carrier steam, methacrylic esters and alkanol and, depending on the alkanol used, have a temperature of about 60 to about 120° C., for example about 70 to about 90° C., when methanol is used. In the distillation column, the methacrylic ester is separated in gaseous form from the vapour constituents which boil at higher temperatures. The high-boiling fractions (mainly methacrylamide, hydroxyisobutyric esters and water) are recycled into the first reaction tank. The methacrylic ester formed is drawn off at the top of the column and cooled by means of a heat exchanger or a battery of two or more heat exchangers. It has been found to be useful in some cases when the methacrylic ester is cooled by means of at least two heat exchangers, in which case a first heat exchanger with water performs the condensation and a cooling to a temperature of about 60 to about 30° C., while a second brine-cooled heat exchanger undertakes a cooling to about 5 to about 15° C. A part-stream from the water-cooled condensate can be introduced as reflux to the columns for concentration control in the column. However, it is equally possible to cool the methacrylic ester formed by means of a battery of more than two heat exchangers. In this case, it is possible, for example, first to undertake a cooling by means of two water-cooled heat exchangers connected in series and then to achieve a further cooling by means of an appropriate brine-cooled heat exchanger.

For example, in the process presented here, the methacrylic ester formed can be cooled in the gaseous state by means of a first heat exchanger with water cooling. Both condensed and uncondensed substances are then passed on into a second heat exchanger, where a further condensation by means of water cooling takes place. At this point, for example, gaseous substances can then be transferred into a separate brine-cooled heat exchanger. The condensate in this brine-cooled heat exchanger is then introduced into the distillate stream, while the remaining gaseous substances can be utilized further or sent to disposal. The methacrylic ester condensate from the second water-cooled heat exchanger is then cooled in a water-cooled or brine-cooled heat exchanger to a temperature of less than 15° C., preferably about 8 to about 12° C. This cooling step can lead to the methacrylic ester formed having a significantly lower content of formic acid than would be the case without the corresponding cooling step. The cooled condensate is then transferred to a phase separator. Here, the organic phase (methacrylic ester) is separated from the aqueous phase. The aqueous phase which, as well as water, may also have a content of organic compounds, especially alkanol, from the distillation step may in principle be used further as desired. However, as already described above, it may be preferred to recycle this mixture of water and organic compounds back into the esterification process by feeding it into the first reaction tank.

The removed organic phase is fed into a scrubber. There, the methacrylic ester is scrubbed with demineralized water. The separated aqueous phase which comprises a mixture of water and organic compounds, especially alkanol, can in turn in principle be used further as desired. However, it is advantageous for economic reasons to recycle this aqueous phase back into the esterification step by feeding it, for example, into the first tank.

Since methacrylic esters have a strong tendency to polymerize, it is in many cases advantageous when care is taken in the esterification of methacrylic acid that such a polymerization is prevented.

In plants for preparing methacrylic acid or methacrylic esters, polymerization often takes place when methacrylic acid or methacrylic ester firstly have a low flow rate, so that local calm zones can form, in which contact lasting over a long period between methacrylic acid or methacrylic ester and a polymerization initiator can be established, which can subsequently lead to polymerization.

In order to prevent such polymerization behaviour, it may be advantageous to optimize the substance flow to the effect that, firstly, the flow rate of the methacrylic ester or of the methacrylic acid is sufficiently high at substantially all points in the system that the number of calm zones is minimized. Furthermore, it may be advantageous to admix the stream of methacrylic acid or methacrylic ester with suitable stabilizers such that polymerization is largely suppressed.

For this purpose, the streams in the process presented here can in principle be admixed with stabilizers such that a minimum level of polymerization takes place in the system itself. To this end, the part of the plant in particular in which the methacrylic acid or the methacrylic ester is present in high concentration during or after the distillation is supplied with appropriate stabilizers.

For example, it has been found to be viable to supply a stabilizer at the top of the distillation column to the stream of methacrylic ester drawn off there. Furthermore, it has been found to be advantageous to flush those parts of the plant in which methacrylic acid or methacrylic ester is circulated with a temperature of more than about 20° C., preferably with a temperature in the range of about 20 to about 120° C., with a solution of stabilizer in methacrylic ester. For example, some of the condensate obtained in the heat exchangers, together with a suitable stabilizer, is recycled into the top of the distillation column such that the column top, on its interior, is sprayed constantly with stabilized methacrylic ester or stabilized methacrylic acid. This is preferably done in such a way that no calm zones can form in the top of the column, at which there is a risk of polymerization of methacrylic acid or methacrylic ester. The heat exchangers themselves may correspondingly likewise be charged with a stabilized solution of methacrylic acid or methacrylic ester in such a way that no calm zones can form here either.

It has also been found to be advantageous in the process presented here when, for example, the offgases comprising carbon monoxide from preceding processes, especially from the amidation step, are passed through the esterification plant together with steam. In this way, the gas mixture is once again purified to remove compounds which can be removed in solid or in liquid form. Secondly, these are collected at a central point and can be sent to further utilization or disposal.

The methacrylic ester obtained or the MMA obtained in the esterification and the subsequent prepurification, or the methacrylic acid obtained, are subsequently sent to a further treatment. The esterification results in dilute sulphuric acid as the remaining residual substance, which can likewise be sent to a further utilization.

Prepurification of the Ester or of the Acid

In the process presented here, the subject matter of the present invention can also be used in connection with a process for prepurifying methacrylic acid or methacrylic ester, as described in the process element which follows. For instance, in principle, crude methacrylic acid or a crude methacrylic ester can be subjected to a further purification in order to arrive at a very pure product. Such a purification which constitutes a further process element can, for example, be in one stage. However, it has been found to be advantageous in many cases when such a purification comprises at least two stages, in which case the low-boiling constituents of the product are removed in a first prepurification as described here. To this end, crude methacrylic ester or crude methacrylic acid is transferred first into a distillation column in which the low-boiling constituents and water can be removed. To this end, the crude methacrylic ester is sent to a distillation column, in which case the addition is performed, for instance, in the upper half of the column. The column bottom is heated with steam, for example, in such a way that a wall temperature of about 50 to about 120° C. is achieved. The purification is performed under reduced pressure. The pressure within the column in the case of the ester is preferably about 100 to about 600 mbar. The pressure within the column in the case of the acid is preferably about 40 to about 300 mbar.

At the top of the column, the low-boiling constituents are removed. In particular, these may, for example, be ether, acetone and methyl formate. The vapours are then condensed by means of one or more heat exchangers. For example, it has been found to be useful in some cases first to perform a condensation by means of two water-cooled heat exchangers connected in series. However, it is equally possible to use only one heat exchanger at this point. The heat exchangers are preferably operated in an upright state to increase the flow rate and in order to prevent the formation of stationary phases. Connected downstream of the water-cooled heat exchanger or the water-cooled heat exchangers may be a brine-cooled heat exchanger, but it is also possible to connect a battery of two or more brine-cooled heat exchangers downstream. In the battery of heat exchangers, the vapours are condensed, provided with stabilizer and, for example, fed to a phase separator. Since the vapours may also contain water, any aqueous phase which occurs is disposed of or sent to a further utilization. An example of a possible further utilization is recycling into an esterification reaction, for example into an esterification reaction as has been described above. In this case, the aqueous phase is preferably recycled into the first esterification tank.

The removed organic phase is fed as reflux into the top of the column. Some of the organic phase can in turn be used to spray the tops of the heat exchangers and the top of the column. Since the removed organic phase is a phase which has been admixed with stabilizer, it is thus possible firstly to effectively prevent the formation of calm zones. Secondly, the presence of the stabilizer brings about further suppression of the polymerization tendency of the vapours removed.

The condensate stream obtained from the heat exchangers is additionally preferably admixed with demineralized water in such a way that sufficient separating action can be achieved in the phase separator.

The gaseous compounds which remain after the condensation in the heat exchanger battery may, preferably by means of steam ejectors as reduced-pressure generators, be subjected once again to a condensation by means of one or more further heat exchangers. It has been found to be advantageous for economic reasons when such a postcondensation condenses not only the gaseous substances from the prepurification. For example, it is possible to feed further gaseous substances to such a postcondensation, as obtained from the main purification of methacrylic esters. The advantage of such a procedure lies, for example, in transferring such a proportion of methacrylic ester which has not been condensed in the main purification stage once more via the phase separator into the purification column in the prepurification. It is thus ensured, for example, that a maximization of yield can take place and minimum losses of methacrylic esters occur. Moreover, the suitable selection of the design and the operation of these further heat exchangers allows the composition of the offgas leaving these heat exchangers, especially the content of low boilers, to be adjusted.

Owing to the feeding of water in the prepurification of the methacrylic ester, the water content in the esterification and the concentration of low-boiling constituents in the crude methyl methacrylate overall can rise continuously. In order to prevent this, it may be advantageous to discharge some of the water fed to the system out of the system, preferably continuously. This discharge can in principle be effected, for example, in an order of magnitude in which water is fed to the system in the prepurification. The aqueous phase separated out in the phase separator typically has a content of organic constituents. It may therefore be advantageous to feed this water to a form of disposal which utilizes this content of organic substances.

For example, it may be advantageous when water thus contaminated with organic substances is fed to the combustion chamber in a sulphuric acid cleavage process. Owing to the oxidizable constituents, its calorific value can still be utilized at least partly. In addition, a possibly expensive disposal of the water contaminated with organic substances is thus often avoided.

Fine Purification of the Methacrylic Ester

For the fine purification of the methacrylic ester, the crude prepurified methacrylic ester is subjected to another distillation. This frees the crude methacrylic ester of its high-boiling constituents with the aid of a distillation column to obtain a pure methacrylic ester. To this end, the crude methacrylic ester is introduced into the lower half of a distillation column in a manner known to those skilled in the art.

The distillation column can in principle correspond to any design which appears to be suitable to those skilled in the art. However, it has been found to be advantageous in many cases for the purity of the resulting product when the distillation column is operated with one or more packings which correspond approximately to the following requirements:

Firstly, just like in the other lines flowed through by methacrylic ester, a minimum level of so-called "dead spaces" should form in the columns. The dead spaces lead to a comparatively long residence time of the methacrylic esters, which promotes their polymerization. This in turn leads to expensive production shutdowns and cleaning of the appropriate parts blocked with polymer. One way of countering the formation of dead spaces is, both by design and by a sufficient operating mode of the columns, to always load them with a sufficient amount of liquid, so that constant flushing of the columns and especially of the column internals such as packings is achieved. For instance, the columns may have spray devices which are designed for the spraying of the column internals. In addition, the column internals may be connected to one another or to the column via interrupted adhesion seams. Such adhesion seams have at least about 2, preferably at least about 5 and more preferably at least about 10 interruptions for 1 m of adhesion seam length. The length of these interruptions may be selected such that they make up at least about 10%, preferably at least about 20% and more preferably at least about 50%, but generally not more than 95% of the adhesion seam length. Another design measure may be that, in the internal regions of the column, especially those which come into contact with the methacrylic esters, less than about 50%, preferably less than about 25% and more preferably less than about 10% of all surfaces, especially of column internals, run horizontally. For example, the stubs which open into the interior of the column may be configured conically or with oblique surfaces. Another measure may consist in keeping the amount of liquid methacrylic ester present in the column bottom as low as possible during the operation of the column, and secondly in preventing overheating of this amount in spite of moderate temperatures and large evaporation surfaces during the evaporation. It may be advantageous in this context that the amount of liquid in the column bottom makes up in the range of about 0.1 to 15% and preferably about 1 to 10% of the total amount of methacrylic ester in the column. The measures proposed in this paragraph may also find use in the distillation of methacrylic acid.

In the purification of the methacrylic ester, its high-boiling constituents are separated from the product by distillation. To this end, the column bottom is heated with steam. The bottom temperature is preferably about 50 to about 80° C., in particular about 60 to about 75° C., with wall temperature of less than about 120° C.

The material obtained in the column bottom is preferably removed continuously and cooled by means of a heat exchanger or a battery of several heat exchangers to a temperature in a range of about 40 to about 80° C., preferably about 40 to about 60° C. and more preferably in a range of about 50 to 60° C.

This material, which comprises predominantly methacrylic ester, hydroxyisobutyric ester, methacrylic acid and stabilizer components, is subsequently, via a storage vessel, for example, disposed of or sent to another use. It has been found to be advantageous in many cases when the material obtained in the column bottom is recycled into the esterification reaction. For example, the material from the column bottom is recycled into the first esterification tank. This gives rise to the advantage that, with a view to a very economically viable method and a very high yield, relatively high-boiling compounds present in the column bottoms are recycled into the esterification reaction.

At the top of the column, the methacrylic ester purified by distillation is withdrawn and cooled by means of a heat exchanger or a battery of two or more heat exchangers. The heat of the vapours can be removed by means of water-cooled heat exchangers or by means of brine-cooled heat exchangers or by means of a combination of the two. It has been found to be useful in some cases when the vapours from the distillation column are transferred into two or more heat exchangers connected in parallel, which are operated by means of water cooling. The uncondensed fractions from the water-cooled heat exchangers can, for example, be introduced into a brine-cooled heat exchanger or a battery of two or more brine-cooled heat exchangers, which may be arranged in series or in parallel. The condensates obtainable from the heat exchangers are introduced into a collecting vessel and sent to a buffer vessel by means of a pump via a further heat exchanger or a battery of two or more further heat exchangers. The condensate stream is cooled, for example, by means of a battery of one or two water-cooled heat exchangers and one or two brine-cooled heat exchangers down to a temperature in a range of about 0 to about 20° C., preferably about 0 to about 15° C. and more preferably in a range of about 2 to 10° C.

A part-stream is withdrawn from the condensate stream and is recycled into the distillation column via the top of the column. The condensate stream can be fed into the top of the column in principle in any way, for example via distributors. However, it may be advantageous when a portion of the condensate stream is fed into the vapour line above the top of the column, for example sprayed in. It is also preferred that this feeding also introduces stabilizer into the top of the column.

A further part-stream of the condensate intended for recycling into the column can, for example, be branched off into the vapour line before introduction and be introduced directly into the top of the column. Here too, it is preferred that this feeding introduces stabilizer into the top of the column. The introduction into the top of the column can be done, for example, in such a way that the interior of the top of the column is sprayed with the condensate such that no calm zones can form in the top of the column at which the methacrylic ester can polymerize. It may additionally be advantageous to add a stabilizer for preventing polymerization to a condensate part-stream which is recycled into the column. This can be done, for example, by adding an appropriate amount of polymerization inhibitor as stabilizer to the condensate part-stream intended for spraying of the top of the column. It has been found to be advantageous in some cases when the condensate part-stream, after the addition of the stabilizer but before entry into the top of the column, passes through a suitable mixing apparatus, preferably a static mixer, in order to achieve very uniform distribution of the stabilizer in the condensate part-stream.

The uncondensable gaseous substances which are obtained in the purification process are, for example, sent to disposal.

The crude product present in the buffer vessel is kept with the aid of a brine cooler at a temperature of about 0 to about 20° C., preferably about 0 to about 15° C. and more preferably in a range of about 2 to 10° C.

In order to remove any further impurities from the product and to arrive at ultrapure methacrylic esters, the product can also be subjected to an absorptive purification stage. It has been found to be useful, for example, when the pure product as a whole, or at least a portion of the pure product, is purified further with the aid of a molecular sieve. Particularly acidic impurities, especially formic acid formed in the preparation process, can thus be removed in a simple manner from the product stream. It has additionally been found to be useful in some cases when the product stream, after passing through the adsorptive purification stage, also passes through one or more filters in order to remove any solids present in the product.

The streams obtained in the workup comprise predominantly polymerizable compounds. In order to, as already described more than once in this text, prevent the formation of calm zones, it has been found to be advantageous in the case of the process described here too when the parts of the plant which come into contact with methacrylic ester are constantly flowed over with methacrylic ester. In a further embodiment of the process presented here, a part-stream of methacrylic ester is therefore withdrawn downstream of the buffer vessel but upstream of the adsorptive purification stage in order to be flushed over the top regions of those heat exchangers which take up the vapours stemming from the distillation column.

The product obtained in the purification stage is subsequently withdrawn from the purification stage with a temperature in a range of about −5 to about 20° C., preferably about 0 to about 15° C. and more preferably in a range of about 2 to 10° C.

Stripping of the Spent Acid

In the process presented here, it may be advisable, for example, in a further process element, to subject the spent sulphuric acid obtained in the process to a purification in order to subsequently recycle it back into the process. In this case, for example, a stream comprising spent sulphuric acid, as can be obtained from the esterification, can be contacted with steam in a flotation vessel. As this is done, at least some of the solids present can be deposited on the surface of the liquid, and these deposited solids can be separated out. The vapours are subsequently condensed in a heat exchanger, preferably with water cooling, cooled and recycled into the esterification reaction.

It has been found to be advantageous in some cases when corrosion is prevented in the heat exchangers and the cooling action is improved further by introducing a mixture of water and organic compounds, as obtained by scrubbing in the course of the esterification in the purification of the methacrylic ester prepared, into the heat exchangers in such a way that the tops of the heat exchangers are sprayed with this mixture. In addition to the corrosion-reducing action and the cooling of the acid in the heat exchanger, this procedure has a further advantage. Material which stems from the esterification (a mixture of water and predominantly methanol) is recycled into the esterification process together with the methacrylic acid and methacrylic ester stemming from exactly this process. In the stripper, the above-described flotation affords mixtures of acid and solids. After their removal, these are sent to any further use or to disposal. It is possible, for example, to incinerate the resulting mixture in a cleavage plant and hence to obtain sulphuric acid again.

The uncondensable gaseous compounds obtained in the stripping are sent to any further use or disposed of.

The plant described here for removing solids from the spent acid and for recycling material from the esterification process into exactly this process can also be performed, for example, twice for reasons of operational reliability. For instance, the two or more flotation vessels can be used offset in time. Since solids can settle out in these vessels, it is advantageous to remove them when the particular flotation vessel is not being used.

The present invention further relates to the use of the methacrylic acid obtainable via the process according to the invention or of the methacrylic ester obtainable by the process according to the invention in fibres, films, coatings, moulding compositions, mouldings, papermaking auxiliaries, leather auxiliaries, flocculants and drilling additives. In addition, the present invention relates to fibres, films, coatings, moulding compositions, mouldings, papermaking auxiliaries, leather auxiliaries, flocculants and drilling additives which are based on a methacrylic acid obtainable by the process according to the invention or a methacrylic ester obtainable by the process according to the invention.

Figure 2:
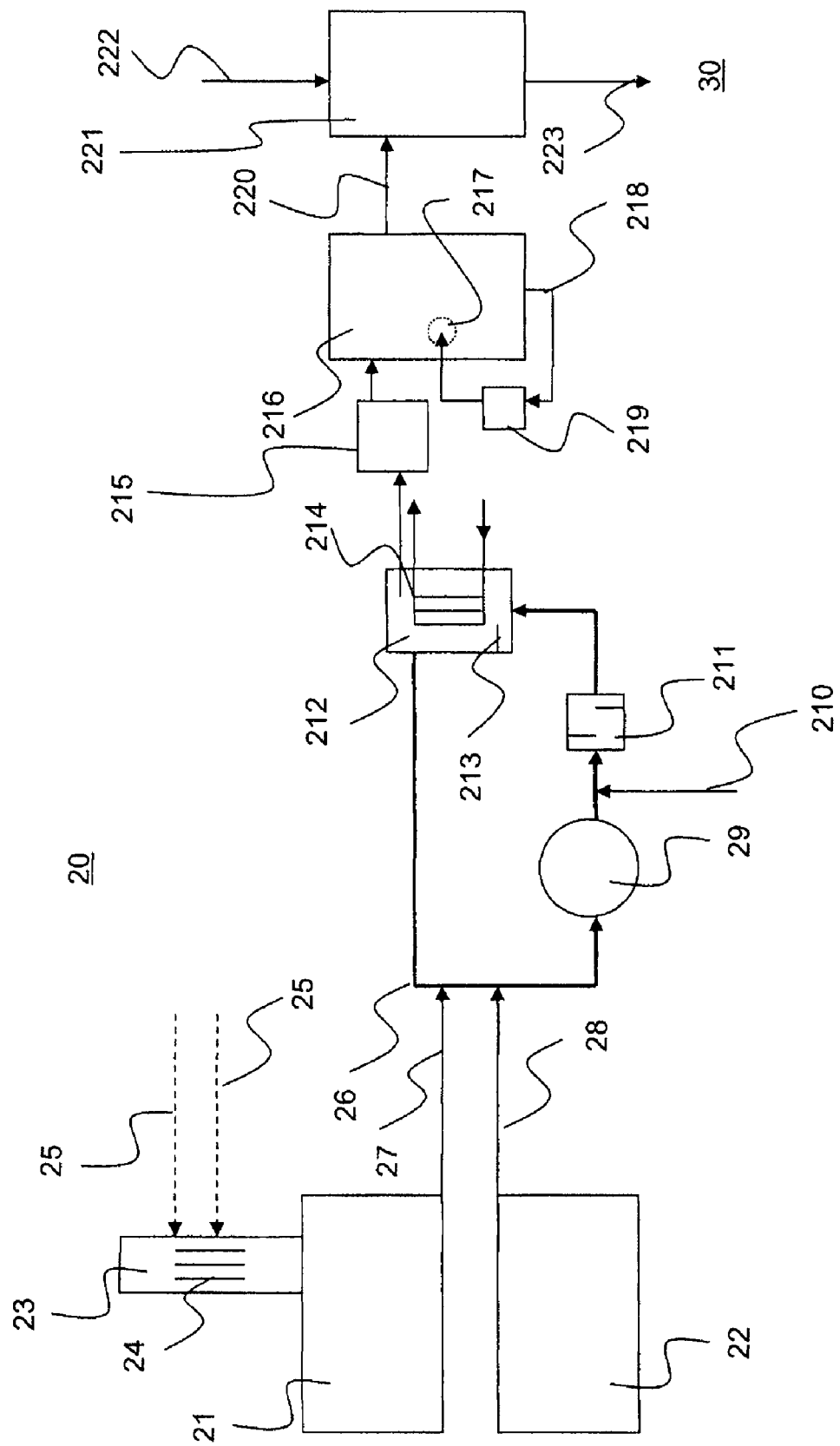
Figure 3:
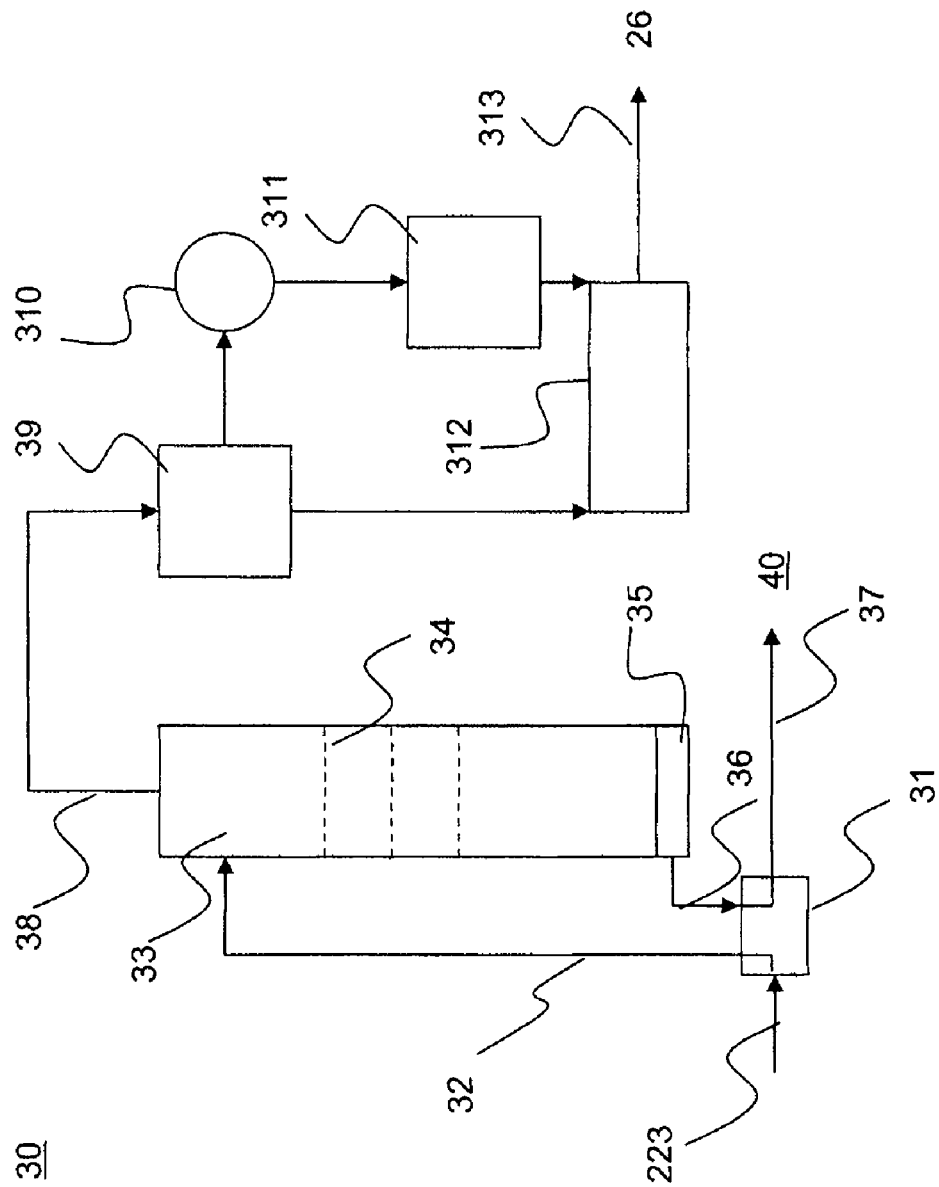
Figure 4:
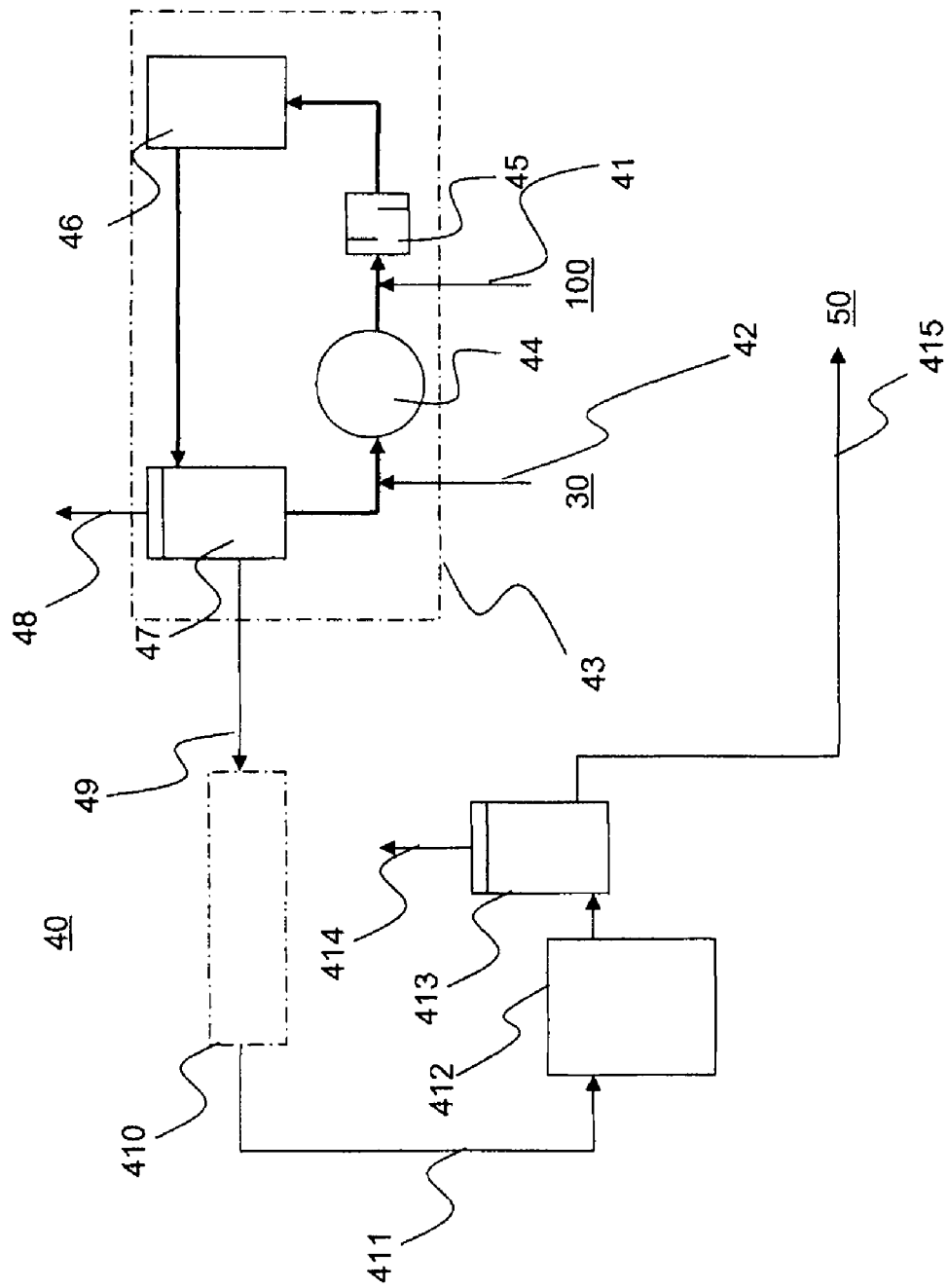
Figure 5:
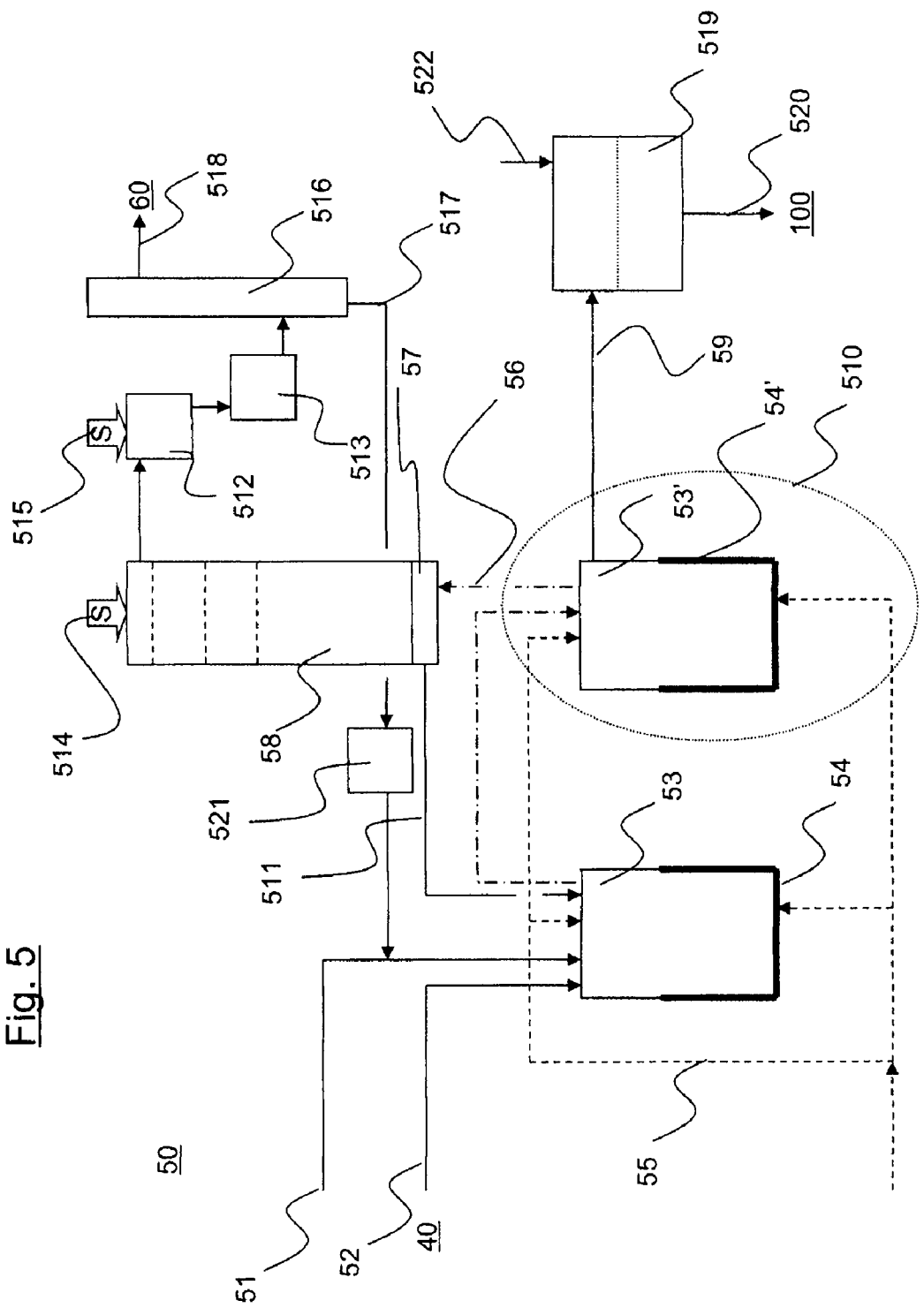
Figure 6:
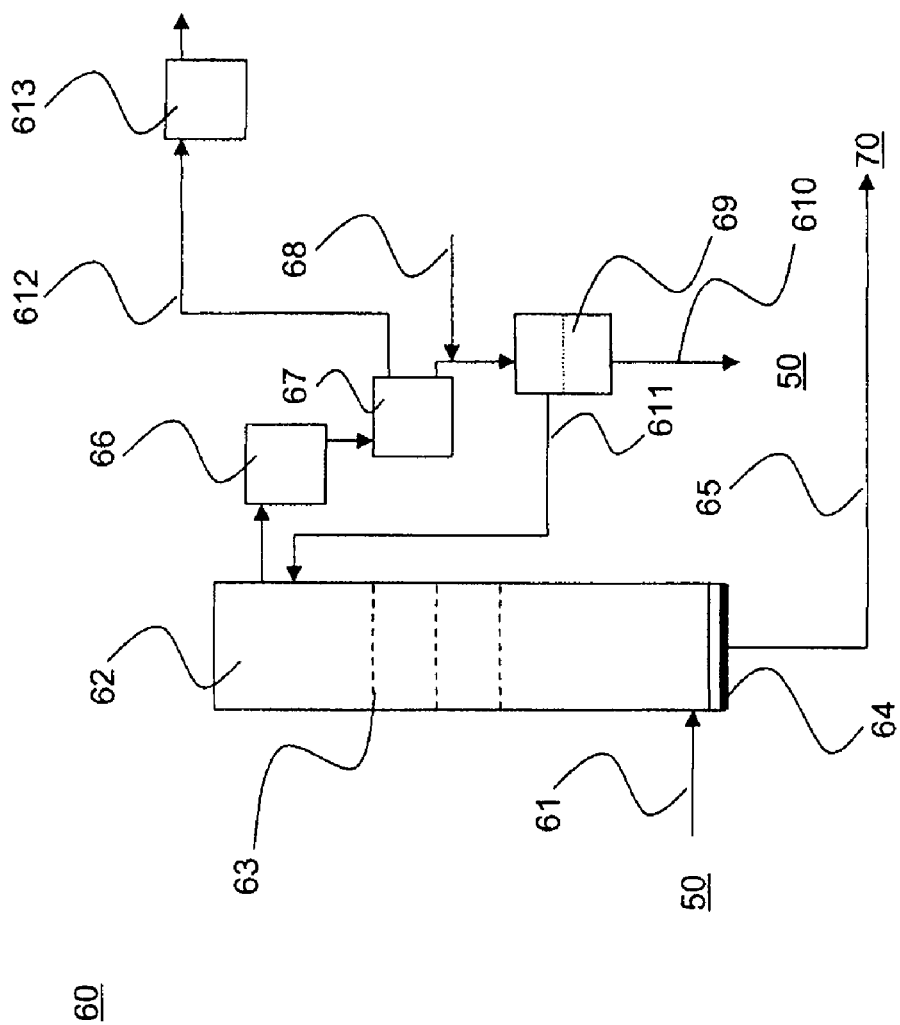
Figure 7:
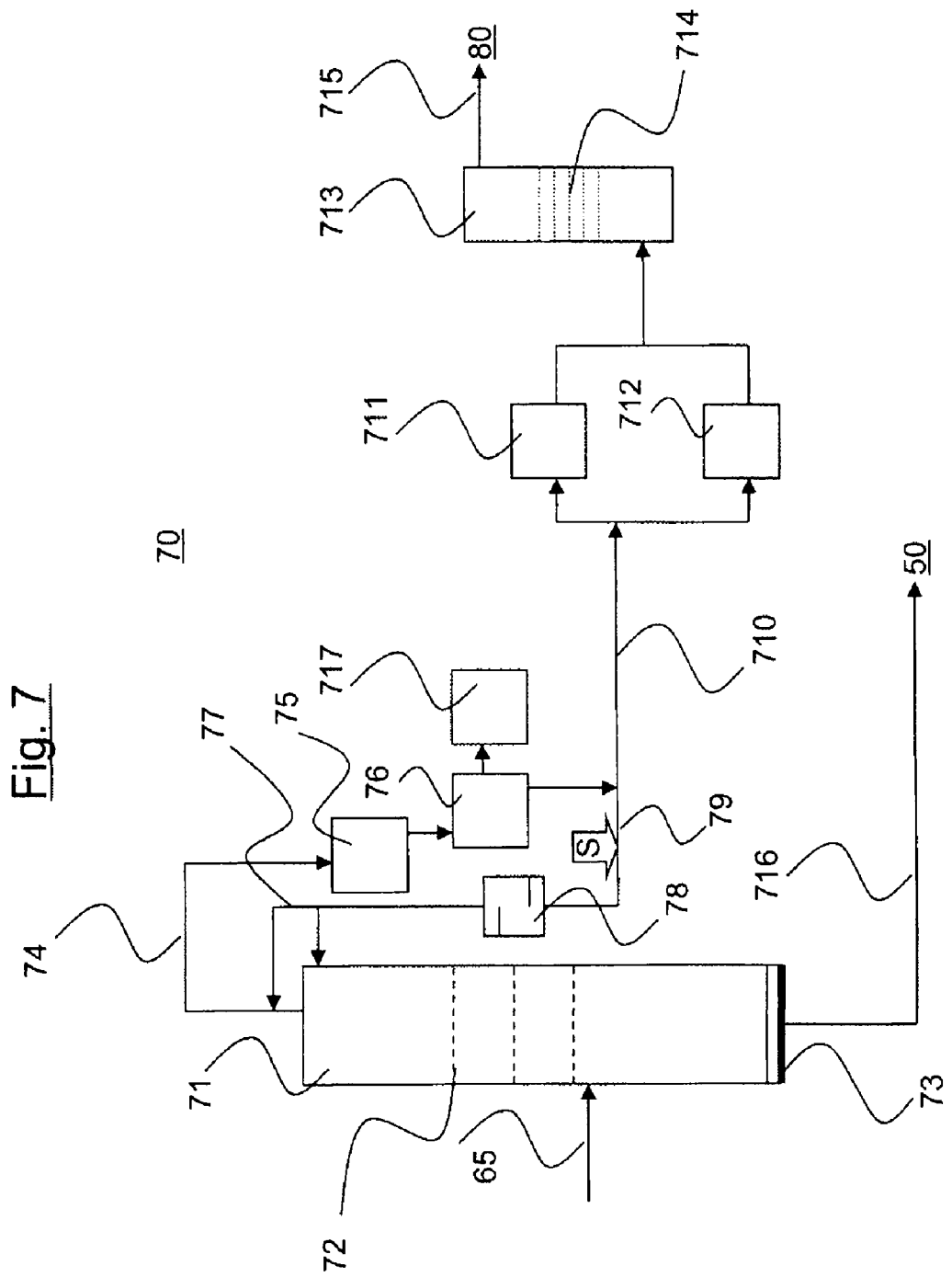

The aforementioned will now be illustrated by way of example with reference to nonlimiting drawings. The drawings show:

FIG. 1: a plant system for preparing and processing methacrylic acid or methyl methacrylate, FIG. 2: a schematic of a plant for preparing acetone cyanohydrin, FIG. 3: a schematic of a workup plant for acetone cyanohydrin, FIG. 4: a schematic of a an amidation plant, FIG. 5: a schematic of an esterification plant, FIG. 6: a schematic of a plant for prepurifying the ester, FIG. 7: the fine purification plant for the ester.

FIG. 1 shows the preferred elements of a plant system 1 for preparing methacrylic acid or methacrylic esters and their further processing products. The plant system 1 has various plants connected to one another usually in a fluid-conducting manner as elements of this system. This plant system includes acetone cyanohydrin preparation 20, followed by acetone cyanohydrin workup 30, followed by an amidation 40, followed by an esterification/hydrolysis 50/50a, followed by a workup for ester or methacrylic acid 60, followed in turn by a fine purification 70, after which the ester, usually methyl methacrylate, or methacrylic acid is present. The pure ester/pure acid thus obtained can be sent to a further processing plant 80. Useful further processing plants 80 include in particular polymerization apparatus and reactors for further organic reactions. In the polymerization reactors, polymethacrylates can be prepared, and, in the reactors for organic reactions, the pure monomers obtained here can be converted to further organic compounds. The further processing plant or the further processing plants 80 is/are followed by a finishing 90. When the further processing products are polymers of methacrylic acid or methacrylic esters, especially methyl methacrylate, they are processed further to give fibres, moulding compositions, especially granules, films, slabs, automobile parts and other mouldings by suitable equipment such as extruders, blown-film extruders, injection-moulding machines, spinneret dies and the like. In addition, the plant system 1 in many cases comprises a sulphuric acid plant 100. For this plant, all sulphuric acid plants which appear to be suitable for this purpose to the person skilled in the art are useful in principle. Reference is made in this context, for example, to Chapter 4, page 89 ff. in "Integrated Pollution Prevention and Control—Draft Reference Document on Best Available Techniques for the Manufacture of Large Volume Inorganic Chemicals—Amino Acids and Fertilizers" obtainable via the European Commission. The sulphuric acid plant 10 is connected to a series of other plants. For instance, the acetone cyanohydrin preparation 20 is supplied with concentrated sulphuric acid via a sulphuric acid line 2. Moreover, a further sulphuric acid line 3 exists between the sulphuric acid plant 100 and the amidation 40. The dilute sulphuric acid also referred to as "Spent Acid" from the esterification 50 (hydrolysis 50a) is transferred to the sulphuric acid plant 100 through the lines for spent sulphuric acid 4 and 5. In the sulphuric acid plant 100, the dilute sulphuric acid can be worked up. The workup of the dilute sulphuric acid can be effected, for example, as described in WO 02/23088 A1 or WO 02/23089 A1. In general, the plants are manufactured from the materials which are familiar to those skilled in the art and appear to be suitable for the particular stresses. Usually, the material is stainless steel which must in particular have exceptional acid resistance. The regions of the plants which are operated with sulphuric acid and especially with concentrated sulphuric acid are additionally lined and protected with ceramic materials or plastics. In addition, the methacrylic acid obtained in the methacrylic acid plant 50a can be fed via a methacrylic acid line 6 to the prepurification 60. It has also been found to be useful to add a stabilizer indicated with "S" in the acetone cyanohydrin preparation 20, the amidation 40, the esterification 50, the hydrolysis 50a, the prepurification 60 and also the end purification 70.

In the acetone cyanohydrin preparation 20 shown in FIG. 2, the acetone is provided in an acetone vessel 21 and the hydrocyanic acid in a hydrocyanic acid vessel 22. The acetone vessel 21 has a scrubbing tower 23 which, in its upper region, has one or more cooling elements 24. A series of offgas lines 25 which stem from various plants in the plant system 1 open into the scrubbing tower 23. The acetone is fed into a loop reactor 26 via the acetone feed 27 and the hydrocyanic acid via the hydrocyanic acid feed 28. Downstream of the hydrocyanic acid feed 28 is disposed a pump 29, followed in turn by a catalyst feed 210 which is followed by a static mixer 211. This is followed by a heat exchanger 212 which has a series of flow resistances 213 and at least one cooling line 214. In the loop reactor 26, the reaction mixture consisting of acetone, hydrocyanic acid and catalyst is conducted in a circuit to a considerable degree, which is indicated by bold lines. From the heat exchanger 212, the reaction mixture is conducted via the flow resistances along the cooling lines 214, and a portion of the circulation stream is passed into a further heat exchanger 215 to which is connected a collecting vessel 216 in which a nozzle 217 is present as part of a cooling circuit 218 with a heat exchanger 219, which keeps the reaction product firstly in motion and secondly cool. Via an outlet 220 which follows the collecting vessel 216, a stabilizer vessel 221 is attached, into which a sulphuric acid feed 222 opens and from which the crude acetone cyanohydrin is conducted through the outlet 223 into the acetone cyanohydrin workup 30.

In FIG. 3, coming from the cyanohydrin preparation 20, the outlet 223 opens into a heat exchanger 31 in which the stream coming from the cyanohydrin preparation 20 is heated. A vapour feed 32 is connected to the heat exchanger 31 and opens out in the upper region, preferably the top region, of a column 33. The column 33 has a multitude of packings 34 which are usually configured as trays. In the lower region of the column 33 is disposed the column bottom 35 from which a bottoms outlet 36 leads into the heat exchanger 31 and heats the streams conducted through the outlet 223 into the heat exchanger 31. A pure product line 37 is connected to the heat exchanger 31, which is followed downstream by the amidation 40. In the top region of the column 33 is disposed a tops outlet 38 which opens into a heat exchanger 39 to which a vacuum pump 310 is connected and opens in turn into a heat exchanger 311. Both the heat exchanger 39 and the heat exchanger 311 are connected via lines to a cooling vessel 312 to which a recycle line 313 is connected and is connected to the loop reactor 26 in the acetone cyanohydrin preparation 20.

The amidation 40 depicted in FIG. 4 first has an acetone cyanohydrin feed 41 and a sulphuric acid feed 42 which open into a loop reactor 43. The acetone cyanohydrin feed 41 connected to the acetone cyanohydrin workup 30 opens into the circuit of the loop reactor 43 downstream of a pump 44 and upstream of a mixer 45. Upstream of this pump 44, the sulphuric acid feed 42 opens out. The mixer 45 is followed downstream by a heat exchanger 46 which in turn opens into a gas separator 47 from which, firstly, a gas outlet 48 and a feed 49 to a further loop reactor 410 exit. The further loop reactor 410 or a third has a comparable construction to the first loop reactor 43. From the further loop reactor 410, a feed 411 enters a heat exchanger 412 which is followed by a gas separator 413, from which, firstly, a gas outlet 414 and an amide line 415 exit, the latter leading to the esterification/hydrolysis 50/MAA plant 50a.

FIG. 5 shows the esterification 50, in which a solvent line 51 which conducts water and organic solvent, and an amide line 52 connected to the amidation 40 open into a tank 53 which is heatable by a tank heater 54. In addition, an alcohol line 55 shown with a broken line opens into the tank 53. The alcohol line 55 opens out both in the upper and in the lower region of the tank 53. The first tank 53 is connected to a further tank 53', which has a further tank heater 54', via an ester vapour line 56 indicated by a line of dashes and dots. This further tank 53' too is connected to the alcohol line 55 both from the bottom and from the top. The ester vapour line 56 is connected to the upper region of the tank 53' and opens into a bottom 57 of a column 58. In addition, a line for dilute sulphuric acid 59 is present in the upper region of the tank 53'. A tank unit 510 encircled in a dotted ellipse is formed from a heatable tank 53 and 54 with alcohol line 55 and ester vapour line 56. It is possible for one, two or more of such tank units to follow in battery-like succession, each of these tank units 510 being connected via the ester vapour line 56 to the bottom 57 of the column 58. From the bottom 57 of the column 58, a high boiler line 511 also leads to the tank 53, in order to feed water and organic solvent back to the esterification. In the upper region, preferably the top, of the column 58, a first heat exchanger 512 followed by a further phase separator 513 are connected via a suitable line. Both at the top of the column 58 and in the first heat exchanger 512, a first stabilizer feed 414 (stabilizer indicated with "S") and a further stabilizer feed 515 may be provided in order to feed an inhibitor or stabilizer which prevents undesired polymerization. Connected to the further phase separator 513 is a scrubber 516 in whose lower region a solvent line 517 exits and opens out in the solvent line 51 via a heat exchanger 521. From the upper region of the scrubber 516, a crude ester line exits and opens into the ester workup 60. The spent acid line 59 exiting from the upper region of the tank 53' or of the tank of the last tank unit 510 opens into a flotation vessel 519 for removal of the solids and constituents insoluble in the spent acid. From the flotation vessel 519, a spent acid outlet 520 enters the sulphuric acid plant 100, and a low boiler vapour line 522 which conducts the low-boiling constituents, for further workup and recycling, enters the esterification.

The ester workup shown in FIG. 6 is connected to the esterification 50 via a crude ester line 61, the crude ester feed 61 opening into the middle region of a vacuum distillation column 62. This column 62 has column internals 63 and a bottom heater 64 arranged in the lower region of the column 62. From the lower region of the column 62 which constitutes the bottom of this column, an ester outlet 65 exits, opens into the ester fine purification 70 and hence feeds the crude ester freed of low boilers to the fine purification. In the upper region of the column 62, usually in the top, a first heat exchanger 66 is connected via an outlet, as are one further heat exchanger or a plurality of heat exchangers 67 which are followed by a phase separator 69. In the phase separator 69, the mixture stemming from the heat exchanger 67 is divided into organic and aqueous constituents, a recycle line 611 in the upper region being connected to the phase separator 69 and opening out in the upper region of the column 62. In the lower region of the separator, a water outlet 610 is present and opens into the esterification 50 in order to feed the water removed back to the esterification. A reduced-pressure generator 613 is connected to the heat exchangers 66 and 67 via a reduced-pressure line 612.

In FIG. 7, the ester outlet 65 stemming from the ester workup 60 opens into a distillation column 71. This comprises a plurality of column internals 71 and, in the lower region of the distillation column 71, a column bottom heater 73. From the top region of the distillation column 71, a pure ester vapour line 74 enters a first heat exchanger 75 which is followed by one (or more) further heat exchangers 76 which are connected to a reduced-pressure generator 717. The outlet of the further heat exchanger 76 has a line from which, firstly, an ester recycle line 77 opens into the upper region, or into the top, of the distillation column 71. The ester recycle line 77 has a stabilizer metering point 79 which is disposed in the ester recycle line 77 upstream of a mixer 78. Secondly, from the line of the further heat exchanger 76, a pure ester outlet 710 exits. An additional heat exchanger 711 and another heat exchanger 712 are connected to this in series connection. These are followed by a molecular sieve vessel 713 which has molecular sieve packings 714. Purified further by the molecular sieve, the ultrapure ester is transferred through the ultrapure ester outlet connected to the molecular sieve vessel into the further processing plant 80.

REFERENCE NUMERAL LIST

1 Plant system
2 Sulphuric acid line
3 Further sulphuric acid line
4 Spent sulphuric acid line—ester
5 Spent sulphuric acid line—acid
6 Methacrylic acid line
20 Acetone cyanohydrin preparation
30 Acetone cyanohydrin workup
40 Amidation
50 Esterification
50a Hydrolysis
60 Prepurification
70 End purification
80 Further processing plant
90 Finishing
100 Sulphuric acid plant
21 Acetone vessel
22 Hydrocyanic acid vessel
23 Scrubbing tower
24 Cooling elements
25 Offgas lines
26 Loop reactor
27 Acetone feed
28 Hydrocyanic acid feed
29 Pump
210 Catalyst feed
211 Mixer
212 Heat exchanger
213 Flow resistance
214 Cooling lines
215 Heat exchanger
216 Collecting vessel
217 Nozzle
218 Cooling circuit
219 Heat exchanger
220 Outlet
221 Stabilizing vessel
222 Sulphuric acid feed
223 Outlet
31 Heat exchanger
32 Vapour feed
33 Column
34 Packings
35 Column bottom with heat exchanger
36 Bottoms outlet
37 Pure product line
38 Tops outlet
39 Heat exchanger
310 Vacuum pump
311 Heat exchanger
312 Cooling vessel
313 Recycle line
41 Acetone cyanohydrin feed
42 Sulphuric acid feed
43 Loop reactor
44 Pump
45 Mixer 46 Heat exchanger
47 Gas separator
48 Gas outlet
49 Feed
410 Further loop reactor
411 Feed
412 Heat exchanger
413 Gas separator
414 Gas outlet
415 Amide line
51 Solvent line
52 Amide line
53 First tank
54 First tank heater
53' Further tank
54' Further tank heater
55 Alcohol line
56 Ester vapour line
57 Column bottom
58 Column
59 Spent acid line
510 Tank unit
511 High boiler line
512 Heat exchanger
513 Phase separator
514 Stabilizer feed
515 Further stabilizer feed
516 Extraction column
517 Solvent line
518 Crude ester line
519 Flotation vessel
520 Spent acid outlet
521 Heat exchanger
522 Low boiler vapour line
61 Crude ester line
62 Vacuum distillation column
63 Column internals
64 Bottom heater
65 Ester outlet
66 Heat exchanger
67 Heat exchanger
68 Water feed
69 Phase separator
610 Water outlet
611 Recycle line
612 Reduced-pressure line
613 Reduced-pressure generator
71 Distillation column
72 Column internals
73 Column bottom heater
74 Pure ester vapour line
75 First heat exchanger
76 Further heat exchanger
77 Ester recycle line
78 Mixer
79 Stabilizer metering point
710 Pure ester outlet
711 Additional heat exchanger
712 Other heat exchanger
713 Molecular sieve vessel
714 Molecular sieve packings
715 Ultrapure ester outlet
716 High boiler line
717 Low boiler draw

The invention claimed is:

1. A process for preparing acetone cyanohydrin, comprising:
reacting a reaction mixture comprising acetone and hydrocyanic acid in the presence of a catalyst in a loop reactor to form acetone cyanohydrin as the reaction product,
said loop reactor comprising
at least one cooling apparatus in which the reaction mixture is cooled,
at least one pump,
at least one mixing apparatus in which the reaction mixture is mixed, and
at least one feed orifice through which hydrocyanic acid, acetone and catalyst are fed, the catalyst being fed in downstream of the feed of acetone or hydrocyanic acid or both.

2. The process according to claim 1, wherein the catalyst is fed in at a point in the loop reactor which is closer to an entry orifice of the reaction mixture into said at least one mixing apparatus than to a feed orifice through which hydrocyanic acid is fed or a feed orifice through which acetone is fed or both feed orifices.

3. The process according to claim 1, wherein the catalyst is fed in at a point in the loop reactor at which the path length of the reaction mixture before entry into an entry orifice of the reaction mixture into said at least one mixing apparatus is at most 30% of the path length that the reaction mixture travels after the feeding of hydrocyanic acid and acetone before entry into an entry orifice of the reaction mixture into said at least one mixing apparatus.

4. The process according to claim 1, wherein the residence time of the catalyst in the reaction mixture between feed and mixing in said at least one mixing apparatus is at most 10 s.

5. The process according to claim 1, wherein the catalyst is fed in continuously or intermittently.

6. The process according to claim 1, wherein the temperature of the reaction mixture in the loop reactor is 11 to 70° C.

7. The process according to claim 1, wherein the catalyst used is an inorganic or an organic base.

8. The process according to claim 1, wherein the catalyst used is an organic amine.

9. The process according to claim 1, wherein the reaction product is withdrawn continuously or intermittently from the loop reactor, the reaction product being cooled to a temperature of 0 to 10° C. in one or more heat exchangers after leaving the loop reactor.

10. The process according to claim 9, wherein the cooled reaction product is admixed with an acid.

11. The process according to claim 10, wherein the reaction product is admixed with sulphuric acid.

12. The process according to claim 10, wherein sulphuric acid with a water content of 0.1 to 8% by weight is used.

13. The process according to claim 1, wherein a sample of the reaction mixture is withdrawn from the loop reactor at least one point and the sample is analyzed spectroscopically.

14. The process according to claim 13, wherein the sampling is effected continuously or intermittently and the sample is fed back to the loop reactor after the analysis.

15. The process according to claim 1, wherein the reaction is performed at a pH of about 6.5 to about 8.

16. A process for preparing acetone cyanohydrin, comprising:
reacting a reaction mixture comprising acetone and hydrocyanic acid in the presence of a catalyst in a loop reactor to form acetone cyanohydrin as the reaction product,
said loop reactor comprising
at least one cooling apparatus in which the reaction mixture is cooled,
at least one pump, at least one mixing apparatus in which the reaction mixture is mixed, and in each case at least one feed orifice through which hydrocyanic acid, acetone and catalyst are fed, withdrawing said reaction product continuously or intermittently from the loop reactor, and cooling the reaction product, after leaving the loop reactor, to a temperature of 0 to 10° C. in one or more heat exchangers and admixing said reaction product with sulphuric acid with a water content of 0.1 to 8% by weight.

17. The process according to claim 16, wherein the catalyst is fed in downstream from the feed of acetone or hydrocyanic acid or both.

18. The process according to claim 16, wherein the catalyst is fed in at a point in the loop reactor which is closer to an entry orifice of the reaction mixture into said at least one mixing apparatus than to a feed orifice through which hydrocyanic acid is fed or a feed orifice through which acetone is fed or both feed orifices.

19. The process according to claim 16, wherein the catalyst is fed in at a point in the loop reactor at which the path length of the reaction mixture before entry into an entry orifice of the reaction mixture into said at least one mixing apparatus is at most 30% of the path length that the reaction mixture travels after the feeding of hydrocyanic acid and acetone before entry into an entry orifice of the reaction mixture into said at least one mixing apparatus.

20. The process according to claim 16, wherein the residence time of the catalyst in the reaction mixture between feed and mixing in said at least one mixing apparatus is at most 10 s.

21. The process according to claim 16, wherein the catalyst is fed in continuously or intermittently.

22. The process according to claim 16, wherein the temperature of the reaction mixture in the loop reactor is 11 to 70° C.

23. The process according to claim 16, wherein the catalyst used is an inorganic base or an organic base.

24. The process according to claim 16, wherein the catalyst used is an organic amine.

25. The process according to claim 16, wherein a sample of the reaction mixture is withdrawn from the loop reactor at least one point and the sample is analyzed spectroscopically.

26. The process according to claim 25, wherein the sampling is effected continuously or intermittently and the sample is fed back to the loop reactor after the analysis.

27. The process according to claim 16, wherein the reaction is performed at a pH of about 6.5 to about 8.

* * * * *